(12) United States Patent
Gong et al.

(10) Patent No.: US 10,955,352 B2
(45) Date of Patent: Mar. 23, 2021

(54) METHOD FOR ASSESSING A STATE OF A LIVING CELL

(71) Applicant: Agency for Science, Technology and Research, Singapore (SG)

(72) Inventors: Tianxun Gong, Singapore (SG); Malini Olivo, Singapore (SG)

(73) Assignee: Agency for Science, Technology and Research, Singapore (SG)

(*) Notice: Subject to any disclaimer, the term of this patent is extended or adjusted under 35 U.S.C. 154(b) by 276 days.

(21) Appl. No.: 16/071,728

(22) PCT Filed: Jan. 12, 2017

(86) PCT No.: PCT/SG2017/050014
§ 371 (c)(1),
(2) Date: Jul. 20, 2018

(87) PCT Pub. No.: WO2017/131583
PCT Pub. Date: Aug. 3, 2017

(65) Prior Publication Data
US 2019/0033218 A1    Jan. 31, 2019

(30) Foreign Application Priority Data
Jan. 29, 2016  (SG) ............................ 10201600721R

(51) Int. Cl.
*G01N 21/65* (2006.01)
*G01N 33/53* (2006.01)
(Continued)

(52) U.S. Cl.
CPC .......... *G01N 21/658* (2013.01); *C07C 233/02* (2013.01); *G01N 33/5308* (2013.01);
(Continued)

(58) Field of Classification Search
CPC .............. B82Y 20/00; C07C 233/02; G01N 2021/656; G01N 21/65; G01N 21/658;
(Continued)

(56) References Cited

U.S. PATENT DOCUMENTS 8,717,558 B2 * 5/2014 Gu ..................... B82Y 20/00
356/301

FOREIGN PATENT DOCUMENTS

| WO | 2005031301 A2 | 4/2005 |
| WO | 2011155901 A1 | 12/2011 |
| WO | 2015038077 A1 | 3/2015 |

OTHER PUBLICATIONS

Zhang et al. Sensors and Actuators B:Chemical, vol. 223, Sep. 21, 2015, pp. 195-201.*

(Continued)

*Primary Examiner* — Maureen Wallenhorst
(74) *Attorney, Agent, or Firm* — Winstead PC

(57) ABSTRACT

A method for assessing a state of a living cell using surface enhanced Raman spectroscopy (SERS) is provided. The method may include modifying one or more living eel Is with an alkyne-containing compound to form one or more modified living cells, mixing the one or more modified living cells with a SERS-active material to form a mixture, injecting the mixture into a conduit defined by an inner wall of a hollow core photonic crystal fiber, and detecting a surface enhanced Raman signal from the mixture in the conduit. In preferred embodiments, the alkyne containing compound is linoleamide alkyne (LLA) for the detection of lipid peroxidation or 4-(dihydroxyborophenyl) acetylene (DBA) for the detection of sialic acid expression in cells, both using gold nanoparticles as the SERS-active material.

17 Claims, 12 Drawing Sheets

(51) Int. Cl.
G01N 33/48 (2006.01)
C07C 233/02 (2006.01)
G02B 6/02 (2006.01)
B82Y 20/00 (2011.01)

(52) U.S. Cl.
CPC .............. B82Y 20/00 (2013.01); G01N 33/48 (2013.01); G01N 2021/656 (2013.01); G02B 6/0229 (2013.01); Y10T 436/24 (2015.01)

(58) Field of Classification Search
CPC .... G01N 33/48; G01N 33/5308; G01N 33/92; G02B 6/0229; Y10T 436/143333; Y10T 436/24
USPC .................................. 436/63, 71, 80, 94, 173
See application file for complete search history.

(56) References Cited

OTHER PUBLICATIONS

Written Opinion of the International Searching Authority for International Application No. PCT/SG2017/050014 dated Mar. 27, 2017, pp. 1-5.
Lin et al., "A Bioorthgonal Raman Reporter Strategy for SERS Detection of Glycans on Live Cells," Angewandte Communications, vol. 52, No. 28, May 23, 2013, pp. 7266-7271.
Doronina-Amitonova et al., "Raman Detection of Cell Proliferation Probes with Antiresonance-Guiding Hollow Fibers," Optics Letters, vol. 37, No. 22, Nov. 7, 2012, pp. 4642-4644.
Khetani et al., "Hollow Core Photonic Crystal Fiber for Monitoring Leukemia Cells Using Surface Enhanced Raman Scattering (SERS)," Optics Express, vol. 23, No. 22, Oct. 28, 2015, pp. 4599-4609.
Hong et al., "Optimal Size of Gold Nanoparticles for Surface-Enhanced Raman Spectroscopy under Different Conditions," Journal of Nanomaterials, vol. 2013, Article No. 790323, Dec. 31, 2013, pp. 1-9.
Chaney et al., "Aligned Silver Nanorod Arrays Produce High Sensitivity Surface-Enhanced Raman Spectroscopy Substrates," Applied Physics Letters, vol. 87, 031908, 2005, pp. 1-3.
Wang et al., "Nanosphere Arrays with Controlled Sub-10-nm Gaps as Surface-Enhanced Raman Spectroscopy Substrates," Journal of the American Chemical Society, vol. 127, 2005, pp. 14992-14993.
Nie et al., "Probing Single Molecules and Single Nanoparticles by Surface-Enhanced Raman Scattering," Science, vol. 275, Feb. 21, 1997, pp. 1102-1106.
Han et al., "Surface-Enhanced Raman Scattering for Protein Detection," Anal Bioanal Chem., vol. 394, Mar. 8, 2009, pp. 1719-1727.
Fabris et al., "SERS Aptatags: New Responsive Metallic Nanostructures for Heterogeneous Protein Detection by Surface Enhanced Raman Spectroscopy," Advanced Functional Materials, vol. 18, 2008, pp. 2518-2525.
Wang et al., "SERS Aptasensor from Nanorod-Nanoparticle Junction for Protein Detection," Chemical Communications, vol. 46, 2010, pp. 613-615.
Kang et al., "Patterned Multiplex Pathogen DNA Detection by Au Particle-on-Wire SERS Sensor," Nano Letters, vol. 10, Mar. 33, 2010, pp. 1189-1193.
Cao et al., "Nanoparticles with Raman Spectroscopic Fingerprints for DNA and RNA Detection," Science, vol. 297, www.sciencemag.org, Aug. 30, 2002, pp. 1536-1540.
Fang et al., "DNA Detection Using Nanostructured SERS Substrates with Rhodamine B as Raman Label," Biosensors and Bioelectronics, vol. 24, 2008, pp. 216-221.
Mitchell et al., "Experimental and Statistical Analysis Methods for Peptide Detection Using Surface-Enhanced Raman Spectroscopy," Journal of Raman Spectroscopy, vol. 39, Jan. 29, 2008, pp. 380-388.
Ryu et al., "Use of Peptide for Selective and Sensitive Detection of an Anthrax Biomarker via Peptide Recognition and Surface-Enhanced Raman Scattering," Journal of Raman Spectroscopy, vol. 41, Jan. 18, 2010, pp. 121-124.

Zhang et al., "Rapid Detection of an Anthrax Biomarker by Surface-Enhanced Raman Spectroscopy," Journal of the American Chemical Society, vol. 127, 2005, pp. 4484-4489.
Li et al., "Three-Dimensional Hierarchical Plasmonic Nano-Architecture Enhanced Surface-Enhanced Raman Scattering Immunosensor for Cancer Biomarker Detection in Blood Plasma," ACS Nano, vol. 7, 2013, pp. 4967-4976.
Ayala et al., "Lipid Peroxidation: Production, Metabolism, and Signaling Mechanisms of Malondialdehyde and 4-Hydroxy-2-Nonenal," Oxidative Medicine and Cellular Longevity, vol. 2014, Article ID 360438, May 8, 2014, pp. 1-31.
Chirico et al., "Lipid Peroxidation in Hyperlipidaemic Patients. A Study of Plasma using an HPLC-Based Thiobarbituric Acid Test," Free Radical Research Communications, 19:1, 1993, pp. 51-57.
Yoshida et al., "Chapter 42: Quantitative Analysis of Lipid Peroxidation Products Using Mass Spectrometry," Sample Preparation in Biological Mass Spectrometry, Springer, Netherlands, 2011, pp. 877-884.
Yin et al., "Simultaneous Analysis of Multiple Lipid Oxidation Products in Vivo by Liquid Chromatographic-Mass Spectrometry (LC-MS)," Free Radicals and Antioxidant Protocols, Humana Press, 2010, pp. 375-386.
David R. Janero, "Malondialdehyde and Thiobarbituric Acid-Reactivity as Diagnostic Indices of Lipid Peroxidation and Peroxidative Tissue Injury," Free Radical Biology & Medicine, vol. 9, 1990, pp. 515-540.
Gérard-Monnier et al., "Reactions of 1-Methyl-2-phenylindole with Malondialdehyde and 4-Hydroxyalkenals. Analytical Applications to a Colorimetric Assay of Lipid Peroxidation," Chemical Research in Toxicology, vol. 11, 1998, pp. 1176-1183.
Fletcher et al., "Measurement of Fluorescent Lipid Peroxidation Products in Biological Systems and Tissues," Analytical Biochemistry, vol. 52, 1973, pp. 1-9.
De Gelder et al., "Reference Database of Raman Spectra of Biological Molecules," Journal of Raman Spectroscopy, vol. 38, 2007, pp. 1133-1147.
Knight, Jonathan C., "Photonic Crystal Fibres," Nature, vol. 424, 2003, pp. 847-851.
Skorobogatiy, Maksim, "Microstructured and Photonic Bandgap Fibers for Applications in the Resonant Bio- and Chemical Sensors," Journal of Sensors, vol. 2009, 2009, pp. 1-21.
Chumanov et al., "Colloidal Metal Films as a Substrate for Surface-Enhanced Spectroscopy," The Journal of Physical Chemistry, vol. 99, 1995, pp. 9466-9471.
Kovacs et al., "Distance Dependence of SERS Enhancement Factor from Langmuir-Blodgett Monolayers on Metal Island Films: Evidence for the Electromagnetic Mechanism," Langmuir, vol. 2, No. 6, Nov./Dec. 1986, pp. 689-694.
Bindoli et al., "Mitochondrial Lipid Peroxidation by Cumene Hydroperoxide and its Prevention by Succinate," Biochimica et Biophysica Acta (BBA)—Bioenergetics, vol. 681, 1982, pp. 496-503.
Weiss et al., "The Mechanism of Cumene Hydroperoxide-Dependent Lipid Peroxidation: The Function of Cytochrome P-450," Archives of Biochemistry and Biophysics, vol. 251, No. 1, Nov. 15, 1986, pp. 348-360.
Kennedy et al., "Carbon-Bonded Silver Nanoparticles: Alkyne-Functionalized Ligands for SERS Imaging of Mammalian Cells," Chemical Communications, vol. 47, 2011, pp. 3156-3158.
Palonpon et al., "Molecular Imaging of Live Cells by Raman Microscopy," Current Opinion in Chemical Biology, vol. 17, 2013, pp. 708-715.
Extended European Search Report for European Patent Application EP 17 74 4653 dated Jul. 23, 2019, pp. 1-11.
Gong et al., "Rapid SERS Monitoring of Lipid-Peroxidation-Derived Protein Modifications in Cells Using Photonic Crystal Fiber Sensor," Journal of Biophotonics, vol. 9, No. 1-2, 2016, pp. 32-37.
Gong et al., "Highly Sensitive SERS Detection and Quantification of Sialic Acid on Single Cell Using Photonic-Crystal Fiber with Gold Nanoparticles," Biosensors and Bioelectronics, vol. 64, Sep. 4, 2014, pp. 227-233.

(56) References Cited

OTHER PUBLICATIONS

Zhang et al., "Design and Fabrication of Side-Channel Photonic Crystal Fiber for Surface Enhanced Raman Scattering Applications," 2015 Conference on Lasers and Electro-Optics (CLEO), May 10, 2015, pp. 1-2.
International Preliminary Report on Patentability issued by the International Bureau of WIPO for International Application No. PCT/SG2017/050014 dated Aug. 9, 2018, pp. 1-7.

* cited by examiner

METHOD FOR ASSESSING A STATE OF A LIVING CELL

CROSS-REFERENCE TO RELATED APPLICATION

This application claims the benefit of priority of Singapore patent application No. 10201600721R filed on 29 Jan. 2016, the content of which is incorporated herein by reference in its entirety for all purposes.

TECHNICAL FIELD

Various embodiments relate to a method for assessing a state of a living cell using surface enhanced Raman spectroscopy (SERS).

BACKGROUND

Living cells are the building blocks of life, as they are the basic unit for all living organisms and must be present for life to exist. By assessing a state of one or more living cells from a living organism, such as detecting presence of certain biomolecules on the living cell and/or monitoring changes in the biomolecules, information such as health conditions about the living organism may be obtained.

An example by which changes in biomolecules on the living cell may be used to assess state of a cell is lipid peroxidation, which refers to the oxidation state of polyunsaturated lipids containing carbon-carbon double bonds. Even though generation of reactive oxygen species (ROS) is a natural consequence of aerobic energy metabolism and is required for a wide range of normal biological processes, when a living cell's antioxidant capacity is unable to keep pace with the production of ROS, the uncontrolled oxidative stress leads to cells, tissues, and organs injury caused by oxidative damage. This damage has been linked to aging as well as the progression of diseases such as atherosclerosis, neurodegenerative disorders, and cancers.

To this end, methods such as high performance liquid chromatography (HPLC), mass spectrometry, fluorescence and colorimetry have been utilized to monitor lipid peroxidation. However, HPLC and mass spectrometry are costly and time consuming, while fluorescence/colorimetric methods involve sophisticated preparation steps.

As a further example, glycans in the form of glycoproteins, glycolipids, glycosaminoglycans or other glycoconjugates may be found on an exterior surface of living cells and play important roles in a variety of cell activities, such as providing structural, modulation, and recognition functions of living cells. In particular, glycans may be correlated with the development and progression of many types of cancer, where changes in the gylcans affect malignant transformation and tumor progression.

Sialic acid is an anionic monosaccharide found at N-glycans, O-glycans and glycosphingolipids, which forms an essential component of glycoprotein and glycolipid on the cellular membrane, and has been used as a tumor associated carbohydrate antigen to identify cancers. For example, overexpression of sialic acid on the surface of cell may indicate malignant and metastatic phenotypes for various types of cancers, while decrease in sialic acid expression may imply erythrocytes of diabetic mellitus. Sialic acid-rich glycoproteins may bind selectin in human organisms such that when they are overexpressed, metastatic cancer cells experience negative charges on their membranes. This may cause repulsion amongst the cells, thereby allowing late-stage cancer cells to enter the blood stream, which further spreads the cancer. In view of the above, accurate monitoring of sialic acid expression on cell surface provides an effective way of studying the malignancy, metastasis of tumor and many other sialic acid related diseases.

Even though efforts have been made to detect and quantify sialic acid using methods such as colorimetric and fluorometric detection, detection sensitivity for colorimetric is low, while fluorometric detection generally suffers from poor discrimination of specific fluorophores, generation of broad emission spectra, and photobleaching. These methods, as well as other methods such as chromatography spectrometry and potentiometric methods, require use of sophisticated equipment and tedious preparations. Furthermore, large amount of cells in the range of about $10^5$ to $10^9$ cells are usually required to sufficiently detect and quantify sialic acid. Development of a simple, reliable and highly sensitive detection and quantification of sialic acid on single cell remains a big challenge.

In view of the above, there exists a need for an improved method for assessing a state of a living cell that overcomes or at least alleviates one or more of the above-mentioned problems.

SUMMARY

According to one aspect, a method for assessing a state of a living cell using surface enhanced Raman spectroscopy (SERS) is provided. The method comprises
a) modifying one or more living cells with an alkyne-containing compound to form one or more modified living cells,
b) mixing the one or more modified living cells with a SERS-active material to form a mixture,
c) injecting the mixture into a conduit defined by an inner wall of a hollow core photonic crystal fiber, and
d) detecting a surface enhanced Raman signal from the mixture in the conduit.

BRIEF DESCRIPTION OF THE DRAWINGS

The invention will be better understood with reference to the detailed description when considered in conjunction with the non-limiting examples and the accompanying drawings, in which.

DETAILED DESCRIPTION

Figure 1A:
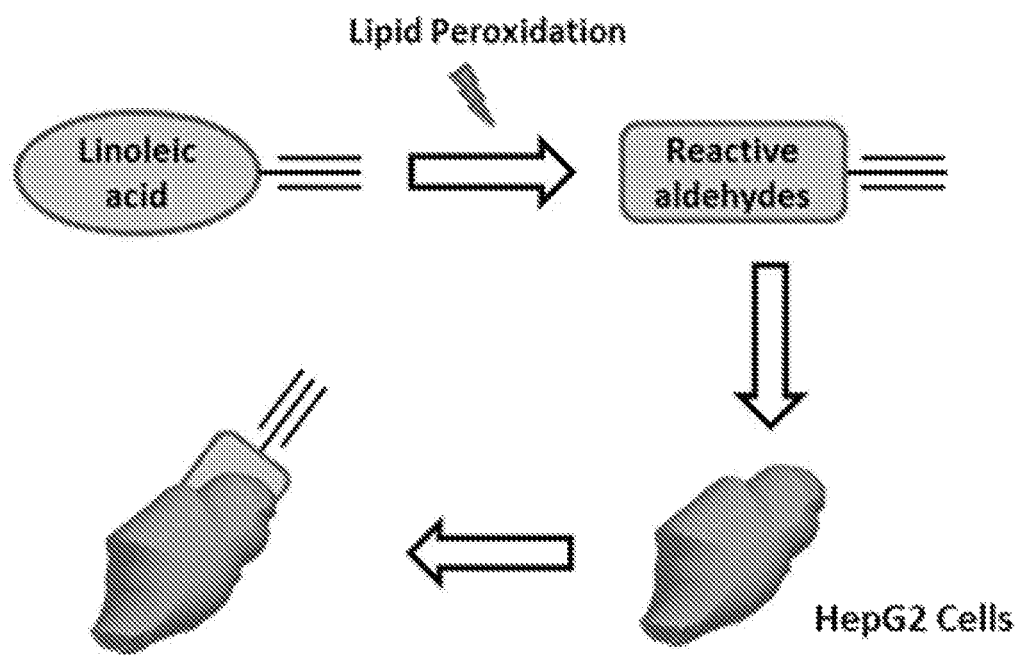
FIG. 1A is a schematic diagram of a hollow core photonic crystal fiber (HC-PCF) sensor according to an embodiment, where linoleamide alkyne (LAA) was tagged to HepG2 cells upon lipid peroxidation.

A surface enhanced Raman spectroscopy (SERS) platform based on hollow core photonic crystal fiber (HC-PCF) may be used to assess a state of a living cell. For example, presence and/or extent of lipid peroxidation derived protein modifications in cells, and presence and/or amount of sialic acid on membrane of cells may be assessed accurately. Alkyne-containing compounds may be added to one or more living cells to modify the living cell(s), such that by mixing a SERS-active material such as noble metal nanoparticles with the modified cells, and loading the resultant mixture into the hollow core of the hollow core photonic crystal fiber, an interference-free alkyne Raman peak from the mixture may be measured using SERS. State of the living cell may be inferred from peak intensity of the alkyne Raman peak, which may in turn provide insight to a condition of the living organism from which the living cell is derived.

With the above in mind, various embodiments disclosed herein refer to a method for assessing a state of a living cell using surface enhanced Raman spectroscopy (SERS).

Surface-enhanced Raman spectroscopy is a form of Raman spectroscopy, which is based on an inelastic light scattering by molecules (the Raman effect). In the Raman scattering process, a photon interacts momentarily with a molecule and is then scattered into surroundings in all directions. During the brief interaction with molecule, photon loses or gains energy which is then detected and analyzed. An important aspect of the Raman scattering is the correlation between the amount of the frequency shifts and the vibrational modes of the molecules. Here, vibrational modes refer to the "manner" in which the molecule vibrates. Since vibrational modes are sensitive to the chemical nature of the molecule, probing molecular vibrations may thus reveal information regarding its chemical geometry. In surface-enhanced Raman spectroscopy, high sensitivity may be achieved by intense enhancement of the local electromagnetic fields in the proximity of a SERS-active material such as a noble metal. Advantageously, its low water background, production of narrower spectral line-widths and no signal bleaching renders its suitability for biological samples analysis.

As mentioned above, the method disclosed herein involves use of surface-enhanced Raman spectroscopy (SERS) to assess a state of a living cell. Living cell refers to a cell of a living organism, and may include a plant cell, an animal cell, or microorganisms such as bacteria, yeast, and fungi. The term "state" as used herein refers to a condition or status of a biological entity such as a living cell. State or condition of a living cell may be assessed or measured by determining a value of an indicator associated with the living cell. For example, assessing a state of the living cell may comprise determining presence and/or extent of lipid peroxidation of the living cell, which allows monitoring of lipid peroxidation derived protein modifications in the living cell. As another example, assessing a state of the living cell may comprise determining presence and/or amount of salic acid on the living cell, which allows monitoring of malignancy and metastasis of tumor, as well as other sialic acid related diseases. The assessment of the state of the living cell may be monitored, for example, by keeping track of a measurement over time, which may be carried out on a systematic, regular, continuous, and/or on-going basis.

The method disclosed herein comprises modifying one or more living cells with an alkyne-containing compound. As used herein, the term "alkyne", otherwise termed as "alkynyl", refers to an alkyl group as defined herein, having at least two carbon atoms and at least one carbon-carbon triple bond. The term "alkyl" refers to a saturated aliphatic hydrocarbon including straight chain, or branched chain groups. Preferably, the alkyl group has 1 to 10 carbon atoms (whenever a numerical range; e.g., "1-10", is stated herein, it means that the group, in this case the alkyl group, may contain 1 carbon atom, 2 carbon atoms, 3 carbon atoms, etc. up to and including 10 carbon atoms). More specifically, it may be a medium size alkyl having 1 to 6 carbon atoms or a lower alkyl having 1 to 4 carbon atoms e. g., methyl, ethyl, n-propyl, isopropyl, butyl, iso-butyl, tert-butyl and the like. The alkyl group may be substituted or unsubstituted. When substituted, the substituent group(s) is one or more, for example one or two groups, individually selected from the group consisting of $C_3$-$C_8$ cycloalkyl, $C_6$-$C_{14}$ aryl, 5-10 membered heteroaryl wherein 1 to 4 ring atoms are independently selected from nitrogen, oxygen or sulfur, 5-10 membered heteroalicyclic wherein 1 to 3 ring atoms are independently nitrogen, oxygen or sulfur, hydroxy, $C_1$-$C_{10}$ alkoxy, $C_3$-$C_8$ cycloalkoxy, aryloxy, mercapto, alkylthio, arylthio, cyano, halo, carbonyl, thiocarbonyl, C-carboxy, O-carboxy, nitro, silyl, sulfinyl, sulfonyl, amino, and —NR$^3$R$^4$ wherein R$^3$ and R$^4$ are independently selected from the group consisting of hydrogen, $C_1$-$C_4$ alkyl, $C_3$-$C_8$ cycloalkyl, $C_6$-$C_{14}$ aryl, carbonyl, acetyl, sulfonyl, amino, and trifluoromethanesulfonyl, or R$^3$ and R$^4$, together with the nitrogen atom to which they are attached, combine to form a five- or six-membered heteroalicyclic ring.

Examples of an alkyne group include, but are not limited to, acetylene, ethynyl, propynyl, butyryl, or pentynyl and their structural isomeric forms.

The term "modifying" as used herein refers to replacing or adding one or more chemical groups to a compound, which may be carried out via physical incorporation or by chemical reaction of a substance containing the one or more chemical groups with the compound. Accordingly, the one or more living cells may be modified with an alkyne-containing compound by physical incorporation of the compound in the living cell(s), or may take place via chemical reaction of the compound with a biomolecule that is present on the living cell(s). In so doing, one or more modified living cells may be formed. In various embodiments, the one or more living cells may be modified with an alkyne-containing compound by covalently attaching the alkyne-containing compound to the one or more living cells.

The alkyne-containing compound may, for example, be selected from the group consisting of an alkyne-modified unsaturated fatty acid, an alkyne-functionalized boronic acid, and combinations thereof.

A fatty acid, otherwise termed herein as a lipid, may be formed of a hydrocarbon chain, usually between 18 to 24 carbons in length, which terminates in a carboxy acid group. The hydrocarbon chain may be saturated or unsaturated, and may be attached to functional groups containing oxygen, halogens, nitrogen or sulfur. The term "unsaturated fatty acid" refers to fatty acids having at least one double bond between carbon atoms of the chain. As a double bond exists, there is the possibility of either a cis or trans geometric isomerism. In embodiments wherein two or more double bonds exist, the term "polyunsaturated fatty acid" may be used.

Examples of unsaturated fatty acid include, but are not limited to, linoleic acid, alpha-linolenic acid, arachidonic acids, eicosapentaenoic acid, docosahexaenoic acid, and combinations thereof. In some embodiments, the unsaturated fatty acid is a naturally occurring fatty acid.

In some embodiments, the alkyne-containing compound is an alkyne-modified unsaturated fatty acid and/or an alkyne-functionalized boronic acid. For example, the alkyne-containing compound may be selected from the group consisting of linoleamide alkyne, 4-(dihydroxyborophenyl) acetylene, and combinations thereof.

Modifying the one or more living cells with the alkyne-containing compound may be carried out using any suitable method. In various embodiments, modifying the one or more living cells with the alkyne-containing compound comprises incubating the one or more living cells with the alkyne-containing compound. The terms "contacting" or "incubating" as used interchangeably herein refer generally to providing access of one component, reagent, analyte or sample to another. The one or more living cells and the alkyne-containing compound may be incubated for a suitable time that allows interaction between them to take place. A suitable amount of time may be dependent on reaction conditions, such as type and amount of the living cells and the alkyne-containing compound, and temperature. A person skilled in the art would be able to determine the appropriate amount of time for any interaction that may take place to occur.

Typically, incubating the one or more living cells with the alkyne-containing compound may take place for a period of time in the order of hours, and be carried out at ambient temperature, which generally refers to a temperature of between about 20° C. to about 40° C. In various embodiments, incubating the one or more living cells with the alkyne-containing compound is carried out for a time period in the range of about 1 hour to about 5 hours, such as about 2 hour to about 5 hours, about 2 hour to about 4 hours, about 2 hours, or about 4 hours. Any unbound or free alkyne-containing compounds may be removed from the modified living cells by washing with a buffer solution such as phosphate-buffered saline.

The method disclosed herein may comprise mixing the one or more modified living cells with a SERS-active material to form a mixture. As mentioned above, in surface-enhanced Raman spectroscopy, high sensitivity may be achieved by intense enhancement of the local electromagnetic fields in the proximity of a SERS-active material, where the Raman signal generated may be enhanced by several orders of magnitude due to the strong surface plasmon resonance.

Examples of a SERS-active material include, but are not limited to, noble metals such as silver, palladium, gold, platinum, iridium, osmium, rhodium, ruthenium; copper, aluminum, or alloys thereof.

In various embodiments, the SERS-active material is in the form of nanoparticles, which may be coated with or are formed entirely of a SERS-active material. For example, the SERS-active nanoparticles may be formed from a non-SERS active material, such as plastic, ceramics, composites, glass or organic polymers, and coated with a SERS-active material such as that mentioned above. The SERS-active nanoparticles may alternatively be formed entirely from a SERS metal selected from the group consisting of a noble metal, copper, aluminum, and alloys thereof. In various embodiments, the SERS-active nanoparticles are coated with or are formed entirely of gold, silver, or alloys thereof.

In specific embodiments, the SERS-active material comprises gold nanoparticles.

Size of the SERS-active nanoparticles may be characterized by their diameter. The term "diameter" as used herein refers to the maximal length of a straight line segment passing through the center of a figure and terminating at the periphery. In the context of a plurality of SERS-active nanoparticles, size of the SERS-active nanoparticles may be characterized by their mean diameter. The term "mean diameter" refers to an average diameter of the nanoparticles, and may be calculated by dividing sum of the diameter of each nanoparticle by the total number of nanoparticles.

In various embodiments, each of the SERS-active nanoparticles has a diameter in the range of about 5 nm to about 250 nm, such as about 40 nm to about 150 nm, about 60 nm to about 100 nm, about 50 nm to about 80 nm, about 60 nm to about 80 nm, about 30 nm to about 70 nm, about 30 nm to about 60 nm, about 50 nm to about 70 nm, or about 60 nm. In specific embodiments, each of the SERS-active nanoparticles has a diameter in the range of about 60 nm to about 100 nm. Advantageously, it has been found by the inventors that SERS-active nanoparticles having a diameter in the range of about 60 nm to about 100 nm provide the greatest enhancement for SERS signals.

The SERS-active nanoparticles may be monodisperse. The term "monodisperse" refers to nanoparticles having a substantially uniform size and shape. In some embodiments, the standard deviation of diameter distribution of the SERS-active nanoparticles is equal to or less than 20% of the mean diameter value, such as equal to or less than 15%, 10%, 5% or 3% of the mean diameter value. In some embodiments, the diameter of the SERS-active nanoparticles is essentially the same for each nanoparticle.

A high concentration of the SERS-active nanoparticles may be present in the mixture. For example, concentration of the SERS-active nanoparticles in the mixture may be in the range of about $1\times10^{10}$ particles/mL to about $1\times10^{12}$ particles/mL, such as about $0.5\times10^{11}$ particles/mL to about $1\times10^{12}$ particles/mL, about $1\times10^{11}$ particles/mL to about $1\times10^{12}$ particles/mL, about $1\times10^{10}$ particles/mL to about $1\times10^{11}$ particles/mL, or about $1\times10^{11}$ particles/mL. A high concentration of SERS-active nanoparticles may be used to ensure that most of the Raman signals may be enhanced, as such enhancement is effective only when Raman tags are located at very close range to the surface of a SERS-active substrate, given that effective enhancement distance is usually less than 100 nm. This is particularly advantageous when SERS analysis is carried out on mammalian cells which have a typical diameter of about 20 µm, since a nanostructured substrate is only able to enhance Raman signal from the bottom of the cell that is in contact with the substrate, resulting in low detection sensitivity. Furthermore, the SERS-active nanoparticles may surround each cell to provide a "three dimensional" enhancement of the Raman signals, as compared to analysis carried out on a conventional SERS-active substrate where only "two dimensional" enhancement is possible.

Concentration of the one or more modified living cells in the mixture may be in the range of about 20,000 cells/mL to about 30,000 cells/mL, such as about 22,000 cells/mL to about 30,000 cells/mL, about 25,000 cells/mL to about 30,000 cells/mL, about 28,000 cells/mL to about 30,000 cells/mL, about 20,000 cells/mL to about 28,000 cells/mL, about 20,000 cells/mL to about 25,000 cells/mL, about 20,000 cells/mL to about 22,000 cells/mL, or about 22,000 cells/mL to about 28,000 cells/mL.

The mixture containing the one or more modified living cells with the SERS-active material is injected into a conduit defined by an inner wall of a hollow core photonic crystal fiber. Injecting the mixture into the conduit may be carried by any suitable method, such as via a syringe.

A hollow core photonic crystal fiber (HC-PCF) is a type of optical fiber, wherein the term "optical fiber" refers to wire that can transfer electromagnetic radiation such as light from one point to another point by internal reflection within the wire. An optical fiber may have a solid core or a hollow core. Solid core fibers are usually adopted as a fiber probe, where one end of the fiber may be tapered by, for example, heating the fiber and applying a tensile force to stretch and to reduce diameter of the fiber. Light from the tapered end may allow for interaction with a sample that is attached to or located near the surface of the tip. As the process to taper the fiber is usually complex, and the light loss from tapered tip is generally large, detection sensitivity using a solid core fiber is therefore limited.

Hollow core photonic crystal fibers, on the other hand, are more favorable as samples may be pumped into the hollow core or a conduit defined by an inner wall of the fiber through one end of the fiber. By irradiating a radiation such as laser into the hollow core or conduit, transmission of the radiation within the hollow core or conduit may interact with the samples through the fiber with improved confinement.

In various embodiments, the conduit of the hollow core photonic crystal fiber is dimensioned to accommodate one modified living cell at each location along its length. For example, a cross-section of the conduit may have a dimension or area that is big enough to hold only one modified living cell at each position along its length.

The conduit may have a circular cross-sectional area. Accordingly, the conduit that is in the hollow photonic crystal fiber may assume a cylindrical shape. In various embodiments, the conduit has a cross-sectional width in the range of about 15 µm to about 25 µm, such as about 18 µm to about 25 µm, about 20 µm to about 25 µm, about 15 µm to about 22 µm, about 15 µm to about 20 µm, about 18 µm to about 22 µm, or about 20 µm.

Figure 1B:
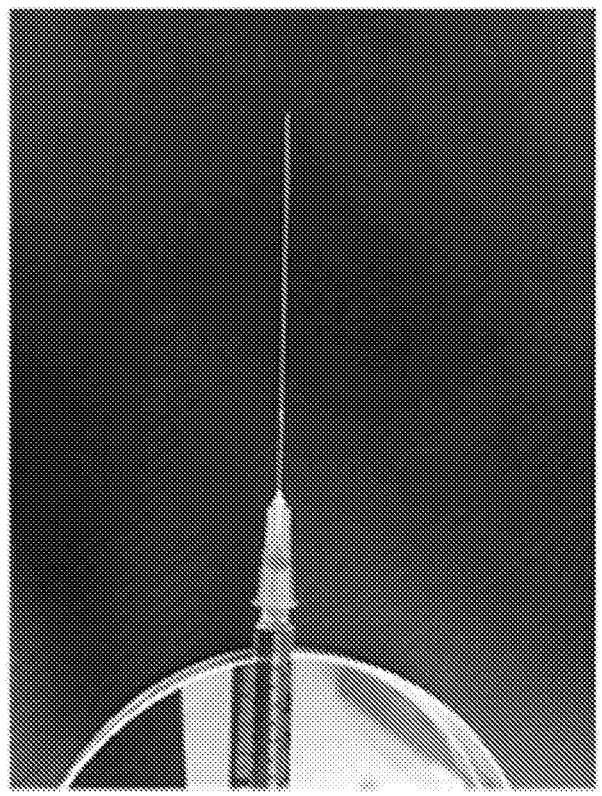
FIG. 1B is a schematic diagram of a HC-PCF sensor according to an embodiment, where LAA tagged cells were mixed with gold nanoparticles (AuNPs) and pumped into the fiber through a syringe.
Figure 1C:
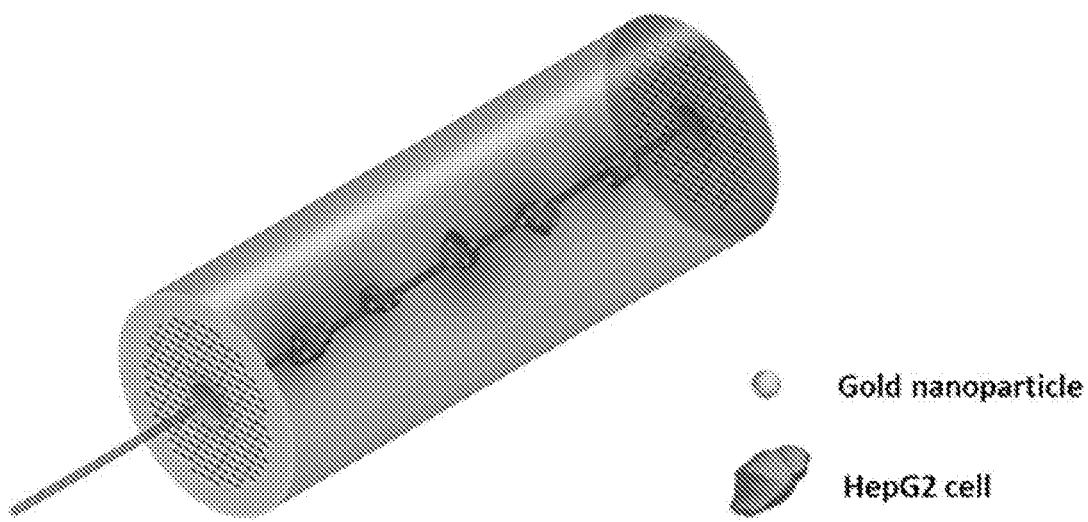
FIG. 1C is a schematic diagram of a HC-PCF sensor according to an embodiment, which depicts SERS detection of LAA tagged cells in fiber.

Depending on the length of the conduit, one, two, three, four, five, or more modified living cells may be arranged in a single file, and may be spaced apart at various positions along the length of the conduit such as that depicted in FIG. 1C. In some embodiments, the conduit is dimensioned to accommodate one modified living cell.

The method disclosed herein comprises detecting a surface enhanced Raman signal from the mixture in the conduit. The term "detecting" as used herein refers to a method of verifying the presence of a given molecule, and includes in vitro as well as in vivo detection. The detection may also be quantitative, such as correlating the detected signal with amount of biomolecules present.

In various embodiment, detecting a surface enhanced Raman signal from the mixture in the conduit comprises directing a radiation such as laser into the conduit for a time period in the range of about 8 seconds to about 12 seconds, such as about 8 seconds to about 10 seconds, about 10 seconds to about 12 seconds, about 9 seconds to about 11 seconds, or about 10 seconds.

The surface enhanced Raman signal may be collected in a backscattering geometry, meaning that the radiation source and detector(s) of the radiation do not have a straight line of sight, but rather rely on the material to be measured to scatter some of the radiation into the detector(s) in order to make a measurement. Advantageously, the hollow core photonic crystal fiber allows signal to be collected from a length of the fiber rather than from a single spot on the fiber. This may result in a much stronger signal intensity while reducing point-to-point variation in intensity at different spots to result in improved accuracy.

As mentioned above, a high concentration of SERS-active nanoparticles may be used to ensure that most of the Raman signals may be enhanced, as such enhancement is effective only when Raman tags are located at very close range to the surface of a SERS-active substrate. In line with the above-mentioned, each living cell in the conduit may be surrounded by a plurality of the SERS-active nanoparticles to provide a "three dimensional" enhancement of the Raman signals. Notably, it has been found by the inventors that the method disclosed herein is highly sensitive due to the improved "three dimensional" enhancement of the Raman signals, and detection limits of as low as 50 nM have been demonstrated.

In various embodiments, detecting a surface enhanced Raman signal from the mixture in the conduit comprises detecting changes in pattern and/or intensity of surface enhanced Raman signal in the region of 1800 $cm^{-1}$ to 2200 $cm^{-1}$, such as about 1900 $cm^{-1}$ to about 2100 $cm^{-1}$, about 2000 $cm^{-1}$ to about 2100 $cm^{-1}$, or about 2000 $cm^{-1}$ to about 2200 $cm^{-1}$. Advantageously, alkyne group possesses a unique SERS signal at a mid-IR region of 1800 $cm^{-1}$ to 2200 $cm^{-1}$ which is isolated from the signature region of Raman peaks characteristic of cells, thus allowing specific identification of the alkyne group without the need to decouple signals.

For example, an alkyne-modified unsaturated fatty acid such as linoleamide alkyne may be used in a method disclosed herein to determine presence and/or extent of lipid peroxidation of the living cell. The alkyne-modified unsaturated fatty acid may be oxidized upon lipid peroxidation, and in so doing, modify the proteins in cells with an alkyne group. By measuring the signature Raman peak of the alkyne group that is in the region of 1800 $cm^{-1}$ to 2200 $cm^{-1}$ at about 2113 $cm^{-1}$ as a function of time, state of lipid peroxidation may be monitored. Peak intensity may reflect extent of lipid peroxidation, where a higher intensity may mean that there is a higher level of lipid peroxidation due to increased oxidation of the alkyne-modified unsaturated fatty acid, to result in a larger number of proteins in cells being modified with an alkyne group.

As another example, an alkyne-functionalized boronic acid such as 4-(dihydroxyborophenyl) acetylene may be used in a method disclosed herein to determine presence and/or amount of salic acid on a living cell. Amount of the salic acid on the living cell may be correlated with surface enhanced Raman signal from the mixture in the conduit. For example, complexing between 4-(dihydroxyborophenyl) acetylene and salic acid molecule on cell membrane may be unity, such that by evaluating number of 4-(dihydroxyborophenyl) acetylene molecules, amount of sialic acid may be quantified. The number of 4-(dihydroxyborophenyl) acetylene molecules may be derived from correlating peak intensity at 2,000 $cm^{-1}$ as a function of number of 4-(dihydroxyborophenyl) acetylene molecules, such as that discussed in Example 14 below.

In some embodiments, the one or more living cells are contained in a sample and the detection is in vitro.

The term "sample", as used herein, refers to an aliquot of material, frequently biological matrices, an aqueous solution or an aqueous suspension derived from biological material. The samples used may vary based on the assay format and the nature of the tissues, cells, extracts or other materials, especially biological materials, to be assayed.

Non-limiting examples of samples include human and animal body fluids such as whole blood, serum, plasma, cerebrospinal fluid, sputum, bronchial washing, bronchial aspirates, urine, semen, lymph fluids and various external secretions of the respiratory, intestinal and genitourinary tracts, tears, saliva, milk, white blood cells, myelomas and the like; biological fluids such as cell culture supernatants; tissue specimens which may or may not be fixed; and cell specimens which may or may not be fixed.

Method according to embodiments disclosed herein may form the basis of detection in biosensors, such as SERS-based biomarker assays for clinical diagnosis and assay for use in laboratory research.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXPERIMENTAL SECTION

Various embodiments relate to a highly sensitive SERS platform to detect lipid peroxidation derived protein modifications in cells using a specialty designed optical fiber. Linoleic acid is the most abundant polyunsaturated fatty acid found in mammals and its lipid peroxidation products likely account for the majority of lipid-derived protein carbonyls. This platform incorporates an alkyne-modified unsaturated fatty acid analog, linoleamide alkyne (LAA) (alkyne-modified linoleic acid), for the detection of lipid-peroxidation in cells. When incubated with cells, LAA incorporates into cellular membranes. Upon lipid peroxidation, LAA is oxidized and produces 9- and 13-hydroperoxy-octadecadienoic acid. These hydroperoxides decompose to multiple $\alpha$, $\beta$-unsaturated aldehydes, which readily modify proteins surrounding them (FIG. 1A). These alkyne-containing modified proteins may subsequently be detected by their alkyne Raman peak at 2113 $cm^{-1}$. As Raman spectra of cell and other biomolecules lie within the region of 400 $cm^{-1}$ to 1800 $cm^{-1}$, the alkyne peak may achieve interference-free detection.

For sensitive SERS detection of cell samples, hollow core photonic crystal fiber (HC-PCF) were adopted. The LAA modified cells were mixed with AuNP solution and pumped into the hollow core of the fiber such that each cell was surrounded volumetrically with large amounts of AuNP. More importantly, light transmitted in the hollow core was able to interact with the sample in the hollow core along the whole length of fiber, greatly increasing the effective enhancement distance.

In contrast, the SERS enhancement for substrate based platform was only effective when Raman tags were located very close to the substrate surface, which was usually less than 100 nm for effective enhancement. In comparison to substrate based SERS, HC-PCF based platform exploited the narrowness of the hollow core to trap cells of micrometer sizes and obtaining prominent SERS spectral profiles.

Example 1

Fiber Preparation for SERS Detection (Embodiment 1)

The HC-PCF fibers were cut into 7-centimeter lengths and both ends were cleaved using an optical fiber cleaver. One end of the fiber was plugged into the tip of a 0.3 mm syringe needle (BD PrecisionGlide) and the connection was sealed with a strong adhesive, ensuring that the liquid sample could be pumped into the fiber through a connected 1 ml tuberculin syringe (BD PrecisionGlide) for SERS measurement (FIG. 1B and FIG. 1C).

Example 2

Cell Culture and Sample Preparation (Embodiment 1)

HepG2 cells were cultured in a six-well plate using Dulbecco's modified eagle medium (DMEM) with 1% penicillin streptomycin (Gibco) and 10% fetal bovine serum (Gibco) in the dark with 5% $CO_2$ at 37° C. until they were 80% confluent. Two microliter of 50 mM of DMSO ((Merck Millipore) dissolved LAA (Life technologies) were added to each well to make a final concentration of 50 μM.

To induce lipid peroxidation, cells were treated with different effective concentrations of cumene hydroperoxide (CH) at 5 μM, 10 μM, 50 μM, 100 μM, and 150 μM in the five wells, respectively. CH was reported and widely used in study as a substance to induce lipid peroxidation. The remaining one well was used as control. After 2 hours of incubation, the cells were washed with 1×PBS for 3 times to remove free LAA. The samples with effective cell concentration of 300,000 cells/mL were prepared by mixing concentrated 60 nm AuNP solution (about $1.04 \times 10^{11}$ particles/mL, BBI solutions) with the harvested cells from these six wells separately. To obtain the Raman spectrum of pure LAA, another sample is prepared by mixing LAA with concentrated 60 nm AuNPs thus the final concentration of LAA is 50 μM.

SERS mapping sample were prepared by HepG2 cells in an eight well chamber slide, the cells were treated with LAA and CH using protocol described above, while the final concentration of LAA and CH in each well was 50 μM and 150 μM, respectively. After 2 hours of incubation and washing, the cells were mixed with concentrated 60 nm AuNPs and then fixed with 4% of formaldehyde for 15 minutes. Thereafter, formaldehyde was removed and rinsed with PBS. The well was removed and a cover slip was fastened with a layer of clean-mount on the slide.

Example 3

SERS Measurement and SERS Mapping
(Embodiment 1)

SERS spectra were obtained using a Raman microscope system (Renishaw InVia) with a Peltier cooled CCD detector and a laser excitation wavelength at 633 nm. The laser was coupled through a 50× objective lens, which was used to collect the Stokes-shifted Raman signal. Rayleigh scattering was blocked with a notch filter.

The HC-PCF was mounted on the microscope stage using a SMA connector and light was coupled into the solid core in fiber end through the objective lens. The SERS signal from cells within the entire length of the HC-PCF was collected in a backscattering geometry. In this study, the fiber was excited with a laser power of about 1.65 mW with 10 s exposure time throughout the measurements. The instrument was calibrated with a silicon standard at a Raman peak of 520 $cm^{-1}$.

SERS mapping experiments were performed in the same Raman microscope system with a laser beam directed to the sample through a 20× objective lens. SERS-mapping of cell sample was conducted by selecting small area on glass slide mounted on microscope stage. Laser excitation at 633 nm wavelength and 3 mW power was used. Mapping measurements at 2113 $cm^{-1}$ for alkyne peak were carried out as raster scans over the specified area (aprox. 50 μm×40 μm) with 1 s integration time.

For SERS detection, the major detection variation usually comes from uneven distribution of hot spots. As a result, only some of the Raman tags close to the hot spots may be enhanced. To avoid this issue, very high concentration of gold nanoparticles was used to ensure most of the Raman tags may be enhanced. More importantly, the fiber based sensor had the advantage of collecting signal from the entire length of fiber rather than on a single spot on a substrate. This reduced point-to-point variation in intensity at different spots, thus achieving accurate monitoring.

Example 4

Detection of CH Induced Lipid Peroxidation
(Embodiment 1)

Figure 2A:
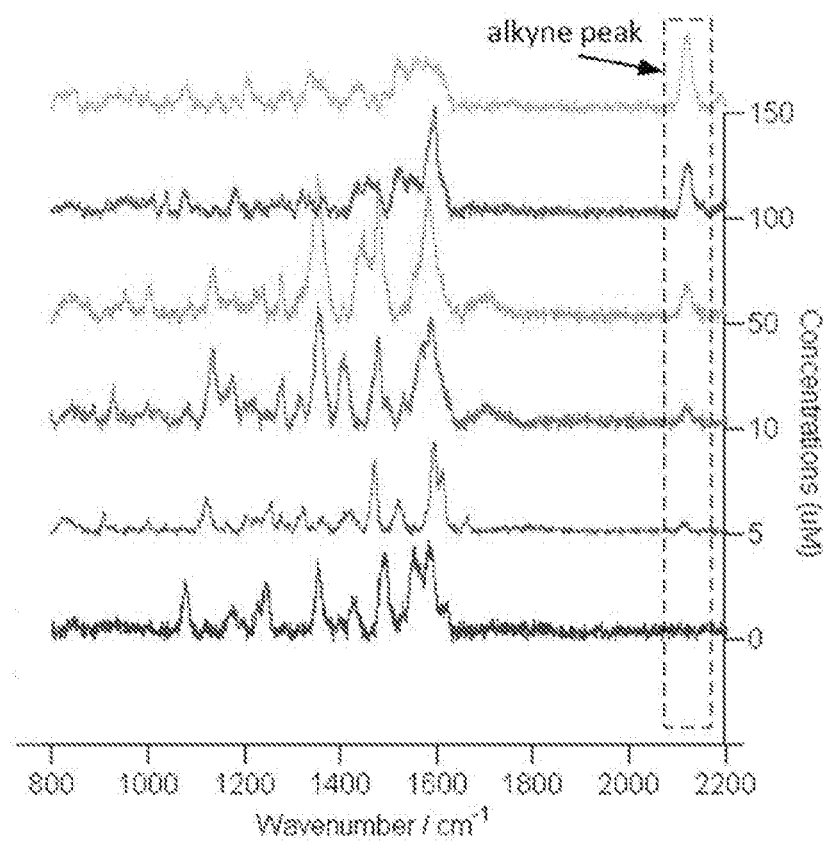
FIG. 2A is a graph showing Raman spectra of cells treated with different concentrations of cumene hydroperoxide (CH).
Figure 2B:
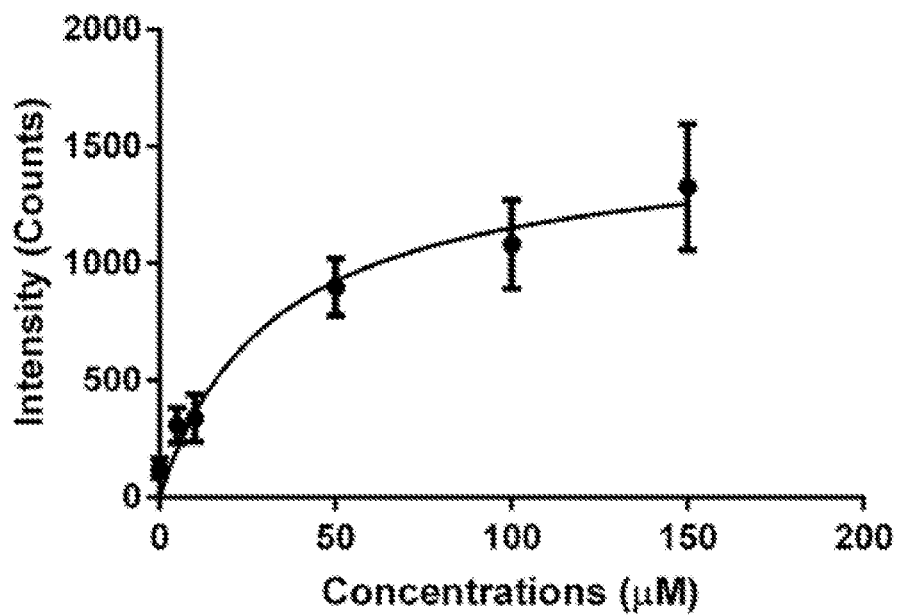
FIG. 2B is a graph showing intensity curve of alkyne Raman peak at 2113 $cm^{-1}$.

In this proof-of-concept study, to demonstrate the feasibility of using SERS to monitor lipid peroxidation in cells induced by CH, HepG2 liver cancer cells were treated with LAA and different concentrations of CH. Upon lipid peroxidation, LAA is oxidized and modify the proteins in cells with alkyne group. By measuring the signature Raman peak of the alkyne group, lipid peroxidation state is monitored. As shown in FIG. 2A, there is an increasing trend of the intensity of alkyne peak with CH concentrations. The significant increase in peak intensity in CH-treated cells indicates elevated lipid peroxidation derived protein modifications and the alkyne peak is detectable for CH concentration as low as 5 μM (FIG. 2B). For cells treated only with LAA, the alkyne peak is negligible due to non-existence of induced lipid peroxidation process, confirming the specificity of the detection system. It is worth noting that the alkynes possess a unique Raman peak which is isolated from the signature region of Raman peaks characteristic of cells, thus enabling specific and interference-free detection.

Example 5

Distribution of LAA in Cells (Embodiment 1)

Figure 3A:
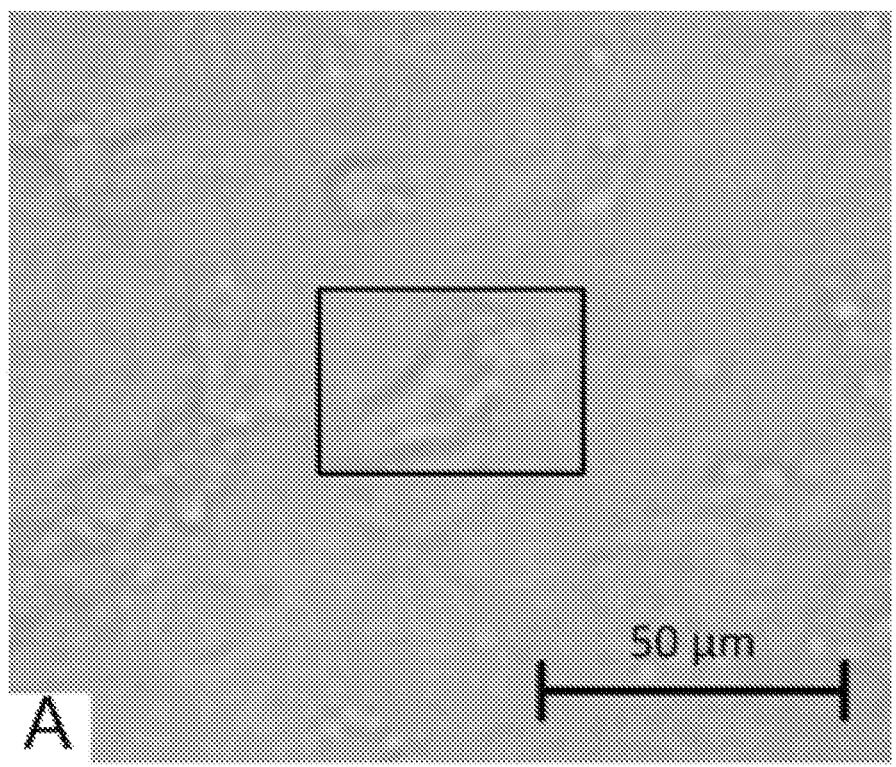
FIG. 3A is an image obtained by Bright field imaging of LAA and CH treated cells, SERS mapping were performed within the rectangle demarcation.

In order to study the specificity of LAA and understand the localization and distribution of alkyne-containing modified proteins in cells, SERS mapping was performed by monitoring the SERS intensity of the alkyne peak at 2113 $cm^{-1}$. The SERS mapping was performed in an area 50 μm×40 μm as shown in FIG. 3A, where one cell was mapped and the mapping focus distances was scanned from −10 μm to 15 μm with a 5 μm steps.

Figure 3B:
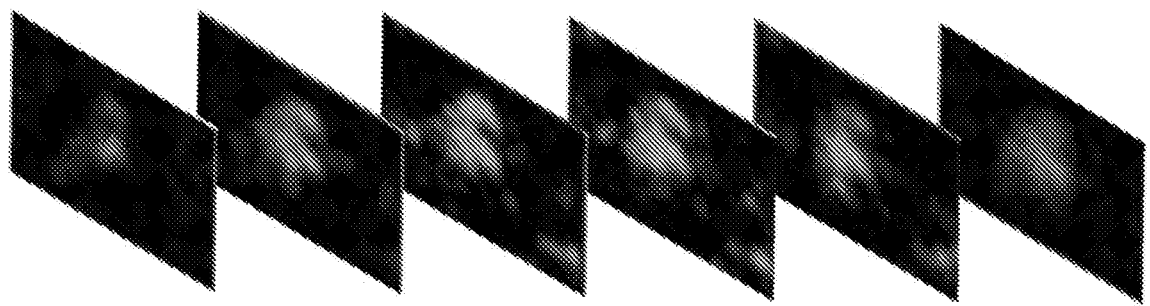
FIG. 3B depicts SERS mapping of intensity of alkyne peak at 2113 $cm^{-1}$ of sample cell in the selected area with focus distances from −10 μm to 15 μm (images from left to right) with a 5 μm steps, the origin focus point 0 μm was set to the center of the cell.

As shown in FIG. 3B, distribution of the red colored regions may be coincided on the cell image. With respect to the background signal, the SERS map indicates that the alkyne signal was localized within the cell, confirming that LAA was able to specifically modify proteins with alkyne group in cell upon lipid peroxidation. This result also indicated that after mixing the cells with high concentration of AuNPs, gold nanoparticles may be found on the surface and inside the cell, thus signal from LAA within a whole cell was vastly enhanced, demonstrating that the sensor concept disclosed herein is capable of monitoring cellular lipid peroxidation.

A HC-PCF based SERS platform capable of accurately monitoring lipid peroxidation derived protein modifications in cells with the use of LAA and AuNPs has been demonstrated herein. The SERS technique exploited the hollow core of HC-PCF fiber to provide high sensitivity, while the LAA enabled specificity and interference-free detection. More importantly, the detection avoided tedious and time consuming preparation and stain procedures, which rendered it possible to rapidly monitor the lipid peroxidation progress in cells. Use of commercial Raman microscopes integrated with the novel designed fiber demonstrated its possible application for rapid fluidic monitoring of lipid peroxidation.

Example 6

Detection and Quantification of Sialic Acid on Single Living Cells (Embodiment 2)

A HC-PCF was used to achieve sensitive detection and quantification of sialic acid on single living cells. The HC-PCF was designed to allow liquid samples to be pumped through the center air hole while light was confined and transmitted in. It was worth noting that the size of the center air hole was comparative with a cell (about 25 µm by 25 µm), thus permitting single cell loading within the channel, thereby making it possible for SERS detection of single living cell. Compare to substrate based SERS detection, the cells were mixed with AuNP solution and pumped into the air channel of HC-PCF, thus each cell is surrounded volumetrically with large amounts of AuNP. This mixture is squeezed in the air channel, therefore achieving '3D' SERS enhancement with extremely high sensitivity which is ideal for sialic acid detection on single cell.

Figure 4A:
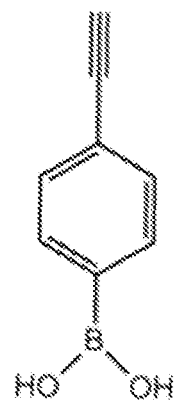
FIG. 4A is a schematic diagram showing chemical structure of 4-(dihydroxyborophenyl) acetylene (DBA).
Figure 4B:
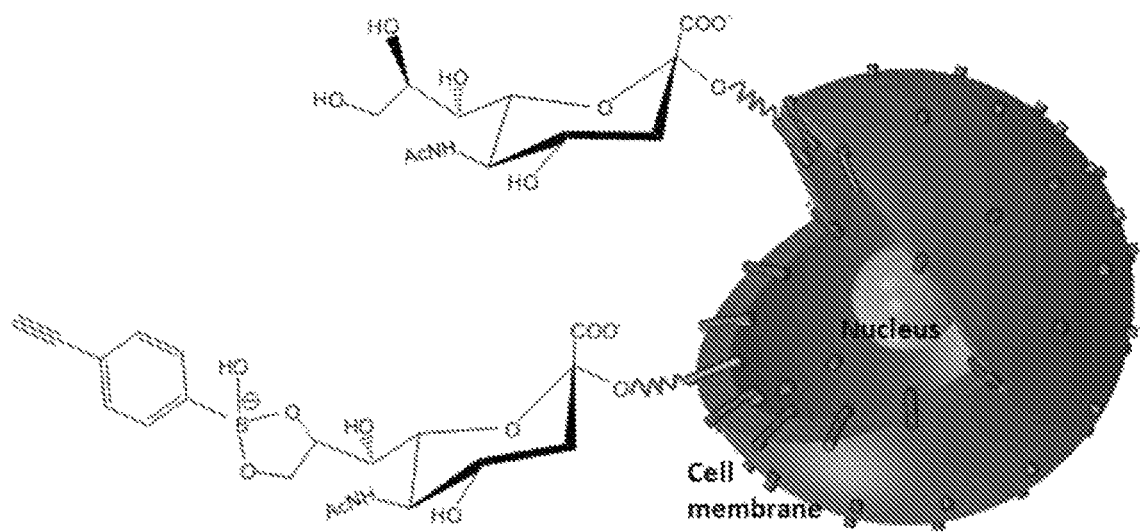
FIG. 4B is a schematic diagram showing sialic acid and DBA bonded sialic acid on cell membrane of living cell at the C-8, 9 diol of sialic acid.

Previous research has shown that phenyl-boronic acid (PBA) can reversibly react with 1,2 or 1,3 diols, which are abundant in glycan structures, to form five- or six-membered cyclic complexes at a pH value around 8 to 9. Kataoka et al. reported that PBA can form favorable binding with sialic acid among common carbohydrates (mannose, glucose, galactose, and sialic acid) on surface of cell at the physiological pH of 7.4, which make it possible for living cell labeling. Recently, Liu et al proposed the use of phenylboronic acid-tagged quantum dots to label sialic acid on cell membrane for fluorescence imaging. It is well studied that Raman spectra of biomolecules and cells lie within the region of 400 $cm^{-1}$ to 1800 $cm^{-1}$. Thus for sensitive SERS biomolecule detection, it is essential that tags should have Raman peak outside of this region in order to avoid signal overlapping. Alkynes which possess a strong SERS peak around the 2,000 $cm^{-1}$ area due to C≡C stretching are suitable for such a platform. 4-(dihydroxyborophenyl) acetylene (DBA) (FIG. 4A) is a commercially available phenylboronic compound with alkyne groups. By exploiting the chemistry between DBA and sialic acid, and the non-interfered alkyne Raman peak, a sialic acid SERS detection can be realized, as shown in FIG. 4B.

In this study, a HC-PCF based system for SERS detection and quantification of sialic acid on single living cancer cells is proposed. SERS intensity of DBA signal with different sizes of AuNP was studied to find the AuNP with optimized SERS enhancement. In order to quantify the amout of sialic acid, different concentrations of DBA solution were pumped in HC-PCF, and SERS intensities were obtained to plot the calibration curve. Sialic acid detection was performed with HeLa cells, as they are known to be sialic acid positive. Four conditions simulating the different levels of sialic acid on cells were tested in the study. Heightened sialic acid level was induced by incubating HeLa cells in prednisolone, and reduced availability of free sialic acid was achieved by incubating cells in competitive phenylboronic acid. Normal HeLa cells treated with and without DBA were used as positive and negative controls, respectively. Finally, darkfield imaging was performed to validate the single cell detection.

Example 7

Simulation (Embodiment 2)

Finite element method (FEM) modeling using commercial software COMSOL Multiphysics was utilized. 3D RF module was adopted to calculate the enhancement factor of AuNP with different sizes. E-field distribution of AuNP was calculated within a square box, while port boundary condition was set at the top and bottom face of the box with 633 nm light excitation at the top propagated along z axis, while E-field was set to vibrate along x-axis. Two faces parallel to the E-field (x-axis) was set to perfect magnetic conductor (PMC) boundary condition and another two faces perpendicular to the E-field is set to perfect electric conductor (PEC) boundary condition.

As AuNP was suspended in water in the study, the refractive index of the subdomain surrounding the AuNP was 1.33, while the refractive index of AuNP was set to 0.19683−j*3.0905. It is generally agreed that the SERS enhancement of AuNP may be approximated by the electromagnetic field enhanced from localized surface plasmon resonance effect. The enhancement factor may be described as follow $$EF_{SERS} \propto \frac{|E_{loc}(\omega_i)|^2 |E_{loc}(\omega_s)|^2}{|E_0(\omega_i)|^2 |E_0(\omega_s)|^2} \quad (1)$$

Interaction of incident light with AuNP surface results in Raman radiation. With the excitation of Raman-active molecules proportional to the square of the local electric field at the excitation frequency, it may be very high at the surface of metallic structures. $E_{loc}(\omega_i)$ and $E_0(\omega_i)$ are the local and incident electric fields at the laser excitation frequency. The emitted Raman radiation is enhanced by the plasmon resonance which is proportional to the local electric fields at the frequency of the Raman scattered frequency. $E_{loc}(\omega_s)$ and $E_0(\omega_s)$ refer to the local and incident electric fields at the Raman scattered frequency. In most cases, because of the weak spectral dependence and ease of calculation, the Raman enhancement factor can be calculated as $$EF_{SERS} = \frac{|E|^4}{|E_0|^4} \quad (2)$$

where E and $E_0$ refer to $E_{loc}(\omega_i)$ and $E_0(\omega_i)$, respectively.

Example 8

Fiber Preparation for SERS Detection (Embodiment 2)

Figure 5A:
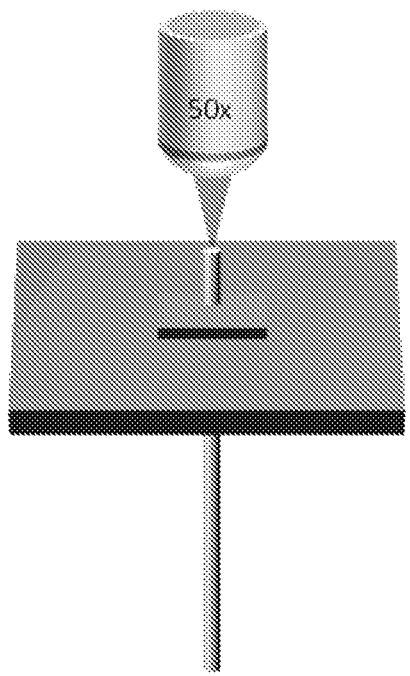
FIG. 5A is a schematic diagram of HC-PCF as a SERS platform for detection of sialic acid on single living cell.
Figure 5B:
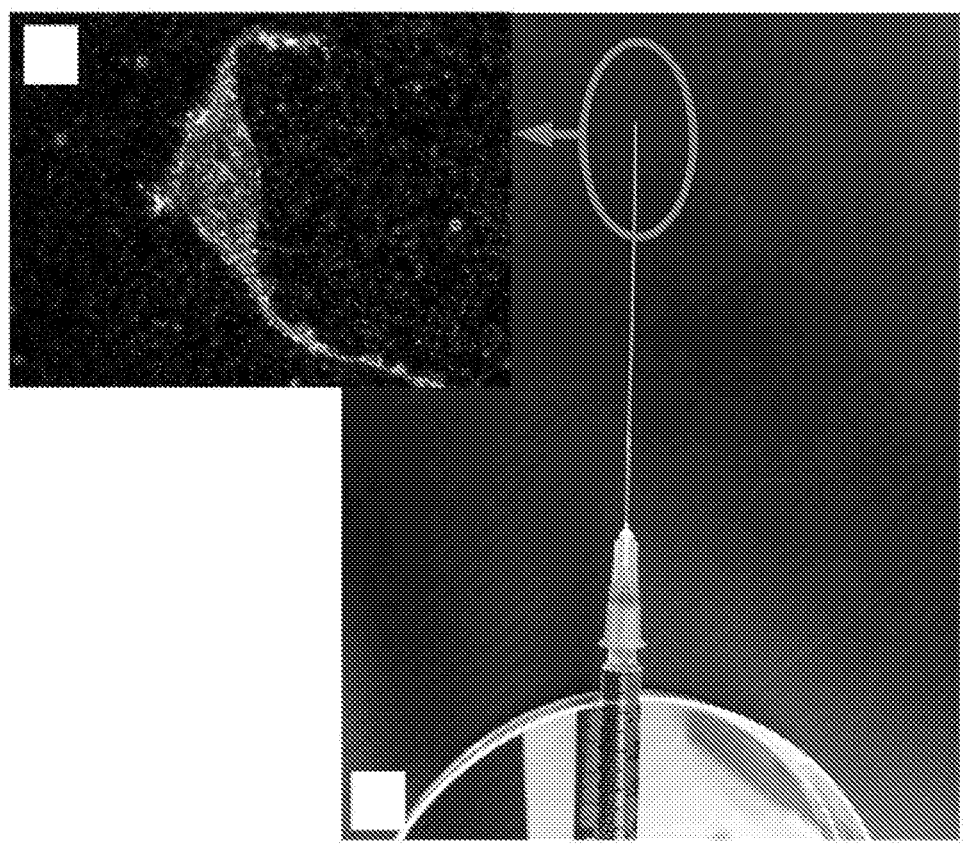
FIG. 5B shows dark-field imaging of single HeLa cell surrounded with 60 nm AuNP pumped out from HC-PCF.

The HC-PCF fibers were cut into 7-centimeter lengths and both ends were cleaved using an optical fiber cleaver. One end of the fiber was plugged into the tip of a 0.3 mm syringe needle (BD PrecisionGlide) and the connection was sealed with a strong adhesive. Therefore, the liquid sample may be pumped into the fiber through a connected 1 ml tuberculin syringe (BD PrecisionGlide) for SERS measurement, as shown in FIG. 5B. It is worth noting that the maximum volume of liquid in the air channel of this fiber segment is about 46.2 nL.

Example 9

HeLa Cell Culture and Varying Sialic Acid Levels (Embodiment 2)

HeLa cells were cultured in Dulbecco's modified eagle medium (DMEM) with 1% penicillin streptomycin (Gibco)

and 10% fetal bovine serum (Gibco) in the dark with 5% $CO_2$ and 37° C. until they were confluent. The cells were then harvested by adding 1×EDTA trypsin of appropriate volume for 4 min, followed by addition of DMEM of double that volume to neutralize the trypsin. The harvested cells were centrifuged at 1,500 rpm for 3 mins. The supernatant was removed and the cells were suspended with DMEM to achieve a cell concentration of 5000 cells/ml. Two milliliter of cell suspension was seeded per well in a six-well plate and allowed to grow for 48 hours.

After incubation, DMEM was removed from each well and the adhered cells were rinsed lightly with 1×PBS which was subsequently removed. Four wells were used in our experiment. In order to reduce the probability of DBA binding onto sites of sialic acid on the surface of the cell membrane, thus mimicking a cell with lowered sialic acid level, 10 mM of phenyl-boronic acid (PBA) (Sigma Aldrich) dissolved in DMEM and 1% DMSO (Merck Millipore) were added to one well (Well A) and left to incubate for 24 hours. 5 μM prednisolone (Sigma Aldrich) dissolved in DMEM and 1% DMSO was added to another well (Well B) to induce the overexpression of sialic acid, and left to incubate for 72 hours. The remaining two wells (Well C and D) were used for positive and negative controls.

Post-incubation washing was performed for all the wells and 10 mM of DBA (Sigma Aldrich) dissolved in DMEM and 1% DMSO was added into wells A, B and C, with incubation time of 4 hours. All four wells were washed twice with 1×PBS to remove excess compounds and unbound cells, and then harvested by trypsinization and centrifugation. Supernatant were removed after centrifugation and the cells are ready for SERS sample preparation.

Example 10

SERS Sample Preparation (Embodiment 2)

For evaluating the size dependence of AuNP on SERS performance, 495 μl of AuNPs of each corresponding size was mixed with DMSO-dissolved DBA (5 μl, 10 mM) separately to obtain DBA of effective concentration of 100 μM. Samples for calibration were made in the same manner, but effective concentrations of DBA is 50 nm, 100 nM, 500 nM, 1 μM, 10 μM and 100 μM. The four types of sialic acid detection samples were prepared by mixing 60 nm AuNP solution with the harvested cells from 4 wells (A, B, C and D) separately, thus the effective concentration of cells in each sample was 20,000 cells/mL.

Example 11

Transmission Electron Microscope (TEM) (Embodiment 2)

Transmission Electron Microscope (TEM) was performed with JEOL JEM-1010 to characterize the shapes and sizes of the AuNP. The TEM specimens were prepared by dropping 2.5 μl of AuNP solution on 200-mesh nickel-coated grids and dried prior to use.

Example 12

SERS Measurement (Embodiment 2)

Figure 5C:
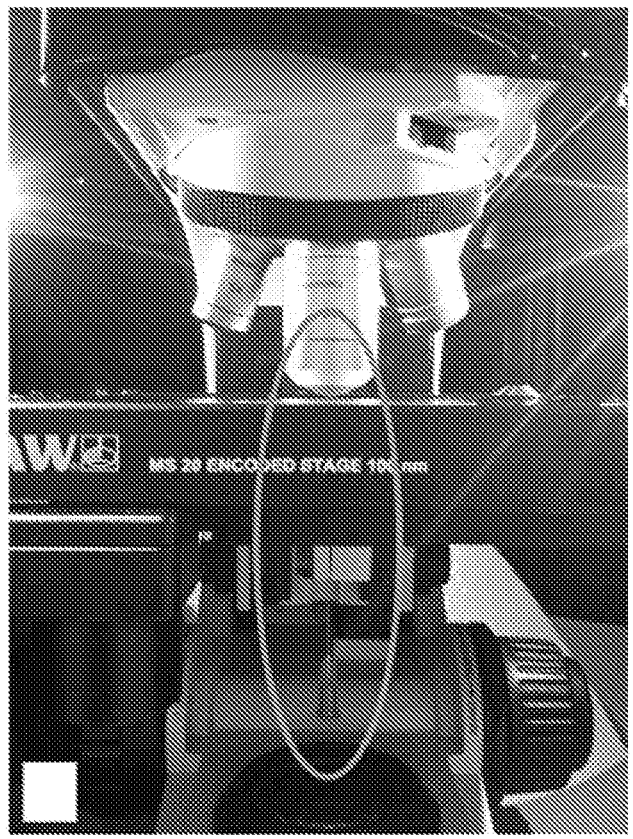
FIG. 5C is an optical image showing HC-PCF mounted on fiber holder in Raman system ready for detection.

SERS spectra were recorded using a Raman microscope system (Renishaw InVia) with a 633 nm excitation laser and equipped with a grating (spectral resolution of about 1.8 $cm^{-1}$). A microscope (Leica) and a CCD detector cooled at −70° C. were connected to the system. The laser was coupled through 50× objective lens, which was used to collect the Stokes-shifted Raman signal. Rayleigh scattering was blocked with a notch filter. In this study, the samples were excited with laser power of about 3.5 mW. The instrument was calibrated with a silicon standard at a Raman peak of 520 $cm^{-1}$. The fiber with liquid sample pumped in was mounted on the microscope stage using a SMA connector and light was coupled into the free-end of the fiber through the objective lens, as shown in FIG. 5A and FIG. 5C. The SERS signal from the entire length of the fiber was collected in a backscattering geometry.

Example 13

Dark-field Imaging (Embodiment 2)

The HeLa cell and AuNP mixture in fiber was pumped out by air using an empty syringe and loaded onto a glass slide. The samples were visualized using an enhanced dark-field illumination system (CytoViva, Auburn, Ala.) attached to a Nikon LV100 microscope. The system consists of a dark-field condenser (CytoViva) attached via a fiber optic light guide to a 24-watt metal halide light source (Solarc Lighting Technology). Images were acquired at 300 ms exposure time using a Nikon objective lens (100×, NA 1.25 and WD 0.23, oil lens) and a Nikon DS-Fi1 camera with associated software (NIS-Elements D).

Example 14

Results and Discussion (Embodiment 2)

AuNP were used in the SERS detection as they were able to dramatically enhance Raman signals. In order to obtain maximum SERS enhancement, the inventors investigated the correlation of DBA intensity enhancement with different diameter of AuNP ranging from 5 to 250 nm in aqueous solutions. The sample solutions were tested on glass slide and in HC-PCF fiber to compare their enhancement capability.

Figure 6A:
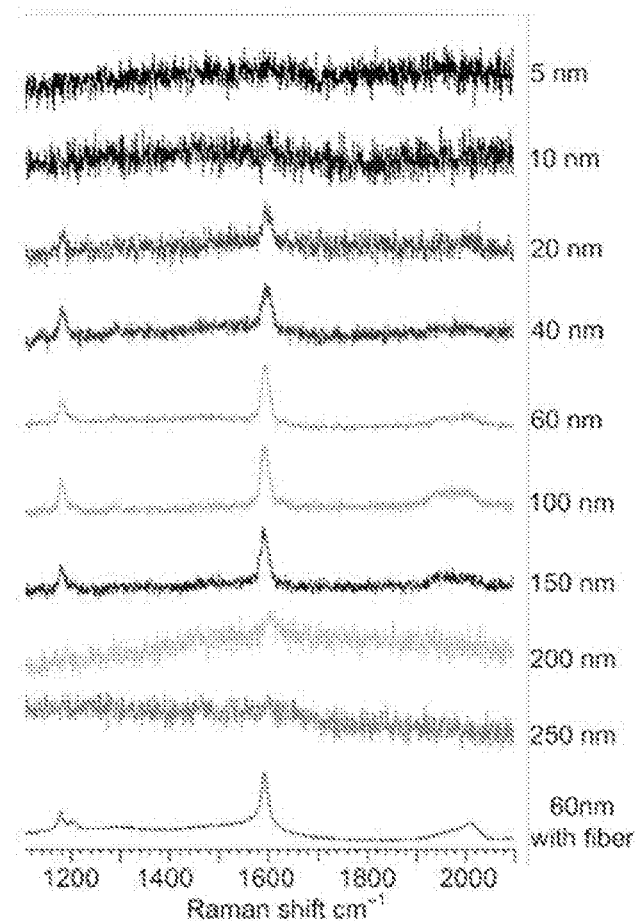
FIG. 6A is a graph showing Raman spectra of 100 μM DBA with different diameter of AuNP tested on glass slide and 100 μM DBA with 60 nm AuNP tested in HC-PCF.
Figure 6B:
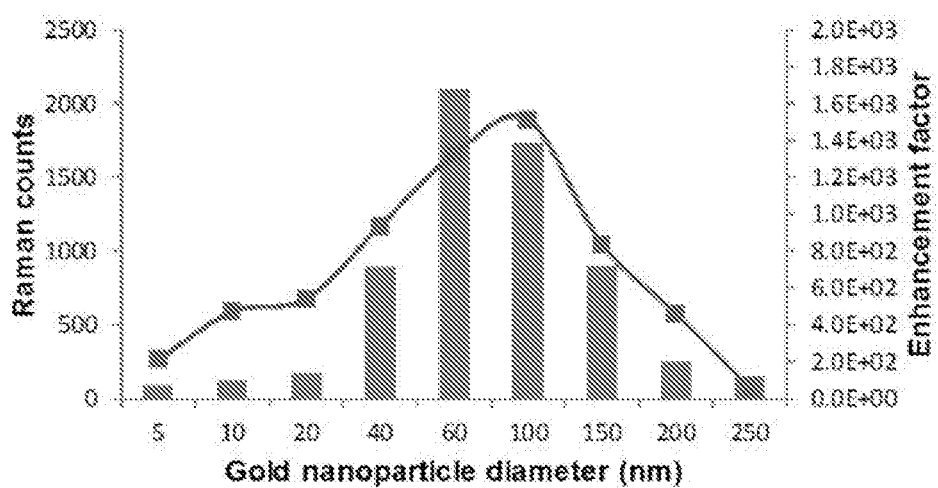
FIG. 6B is a graph showing Raman intensity of 100 μM DBA with different diameter of AuNP and calculated Raman enhancement factor for different diameter of AuNP.
Figure 6C:
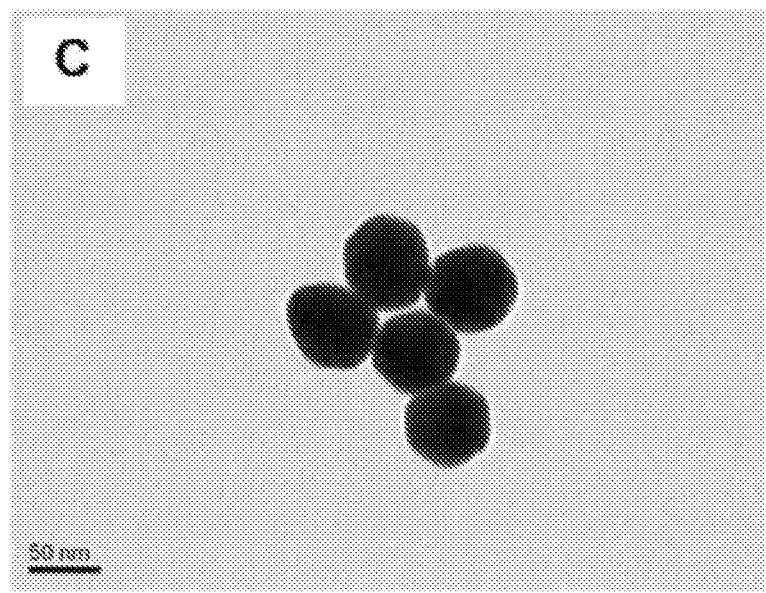
FIG. 6C is a transmission electron microscopy (TEM) image of 60 nm AuNP.
Figure 6D:
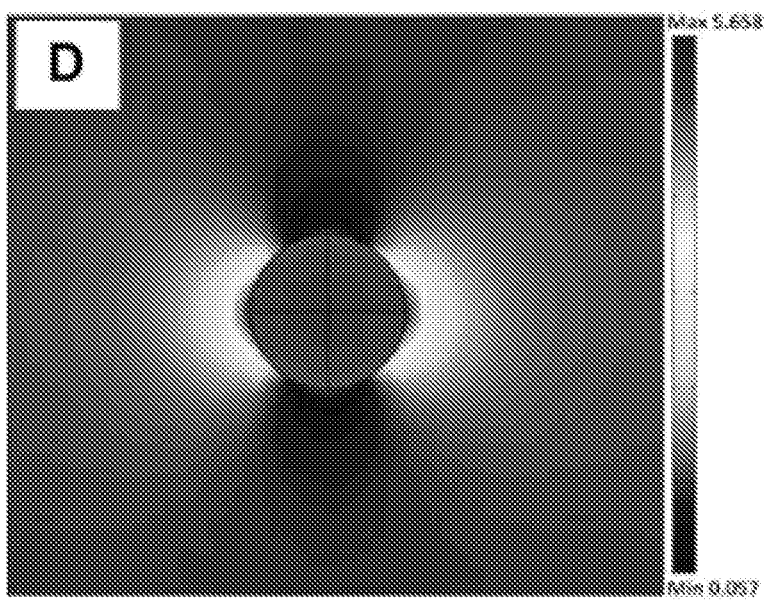
FIG. 6D is an image showing calculated $|E|/|E_0|$ of 60 nm AuNP under 633 nm light excitation.

As shown in FIG. 6A, AuNP with diameter at 60 nm (FIG. 6C) and 100 nm give highest enhancement for DBA signal. This experimental result correlated well with the simulation results, as shown in FIG. 6B. As for simulation, the inventors only calculated the enhancement factors of single AuNP (as shown in FIG. 6D) without considering the effect of chemical bonds and multiple AuNP, thus accounting for the slight difference between calculation and experimental results.

It is worth noting that the signals obtained from glass slide were much weaker than that those of HC-PCF fiber. This was because laser light was scattered diffusely after impinging upon the sample on glass slide, thus only a portion of the scattered light was able to be collected by the objective lens. While for HC-PCF, the scattered light may be conducted back to the objective lens. More importantly, the laser light was able to interact with sample solution for a much longer distance through the whole length of fiber than on glass slide, therefore resulting in much stronger signal intensity.

Since the complexing between DBA molecule to sialic acid molecule was unity on cell membrane, by evaluating the number of DBA molecules, the inventors were able to quantify the amount of sialic acid. One effective way to quantify sialic acid is to perform a Raman intensity calibration study for DBA with different concentrations.

Figure 7:
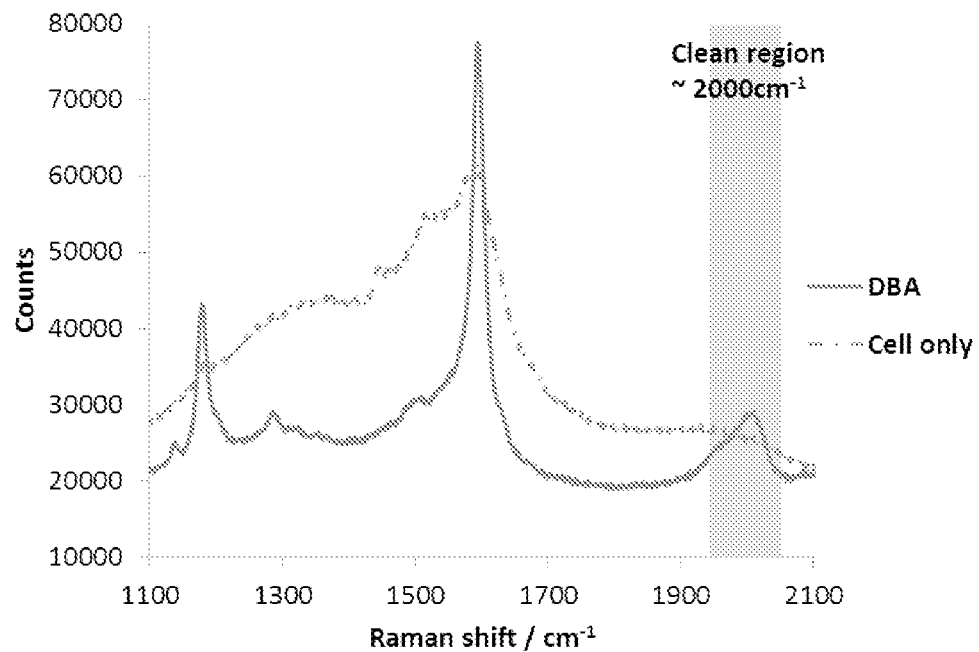
FIG. 7 is a graph showing Raman spectra of 100 μM DBA with 60 nm AuNP (red line) and HeLa cell (blue line) in HC-PCF.

As shown in FIG. 7, DBA has three major Raman peaks at 1,174 cm$^{-1}$, 1,592 cm$^{-1}$ and 2,000 cm$^{-1}$ that may potentially be used for intensity calibration. However, Raman signal from cells overlaps with DBA signal below 1800 cm$^{-1}$, therefore interfering with the intensities for DBA peak at 1,174 cm$^{-1}$ and 1,592 cm$^{-1}$, resulting in incorrect detection value. On the contrary, DBA peak at 2,000 cm$^{-1}$ from its alkyne functional group is beyond the aforementioned range and within a relative clean region. Therefore, it is the choice peak for the calibration study.

Figure 8A:
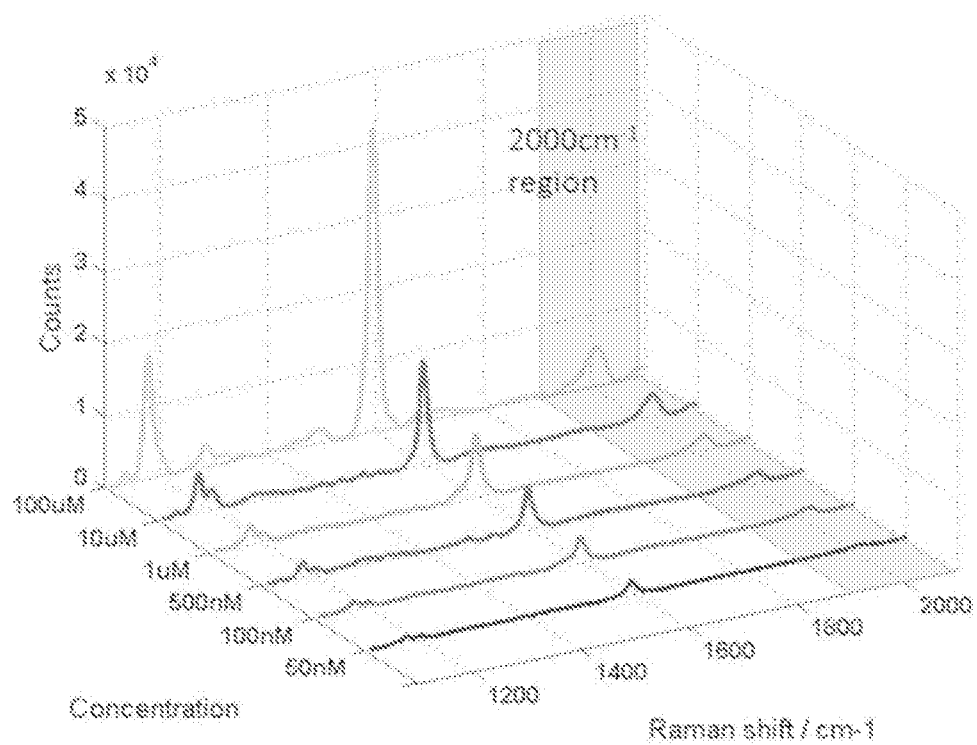
FIG. 8A is a graph showing Raman spectra of different concentrations of DBA with 60 nm AuNP in HC-PCF.
Figure 8B:
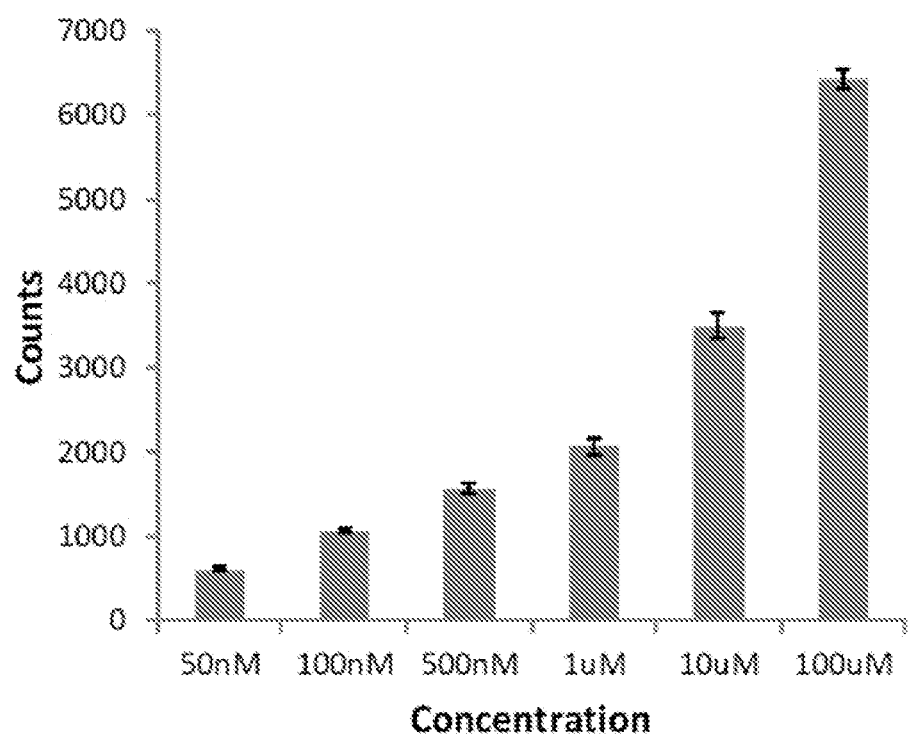
FIG. 8B is a graph showing calibration plot of 2,000 cm$^{-1}$ peak intensity for different concentrations of DBA with 60 nm AuNP in HC-PCF.

In the calibration study, samples with different DBA concentrations were pumped into the FIC-PCF for SERS measurement. As shown in FIG. 8A, the Raman intensity of DBA spectra increased with higher concentrations. Calibration curve for intensity of 2,000 cm$^{-1}$ peak was plotted in FIG. 8B. It is worth noting that with the strong '3D' enhancement from the HC-PCF fiber disclosed herein, the detection limit of the 2000 cm$^{-1}$ peak of DBA was found to as low as 50 nM. As the amount of sialic acid on single cell is very low, our system makes it possible to achieve this highly sensitive detection. From DBA concentrations ranging from 50 nM to 100 μM, the number of DBA molecules for each liquid sample in the 46.2 nL air channel of the fiber were 2.31 fmoles, 4.62 fmoles, 23.1 fmoles, 46.2 fmoles, 462 fmoles and 4.62 pmoles, respectively.

In order to evaluate the sensitivity of the detection with changes of sialic acid level, the inventors manipulated the sialic acid level by incubating cell in the presence of prednisolone (which encourages production of sialic acid) and PBA (which binds sialic acid competitively with DBA, depending on the sequence in which the compounds were added to the cells).

The sialic acid level in the HeLa cells may be elevated through treatment with prednisolone, a chemical which can inhibit the shedding of surface sialopeptides into the medium. Normal HeLa cells tagged with and without DBA were used for positive (Sialic acid) and negative (Cell only) controls. As shown in FIG. 5A to FIG. 5C, these samples were pumped by syringe into the HC-PCF and mounted on the stage of Raman system by a fiber connector, therefore enabling the transmission of laser light into the fiber for SERS detection.

It is worth noting that the inventors fixed the concentration of cells in each sample to be 20,000 cells/mL, and the cells were uniformly dispersed before pumping them into the fiber. The resultant estimated number of cells in a 46.2 nL air channel of the fiber was less than one (about 0.862). This ensured that the detection of sialic acid was restricted to single cell.

To further validate the above assumption, the inventors use an empty syringe to pump out the liquid sample from fiber on to a glass slide after SERS measurement. Dark-field imaging was used to exam the number of cells in such sample, as shown in FIG. 5B. It was observed that only one HeLa cell was found in the field.

Figure 9:
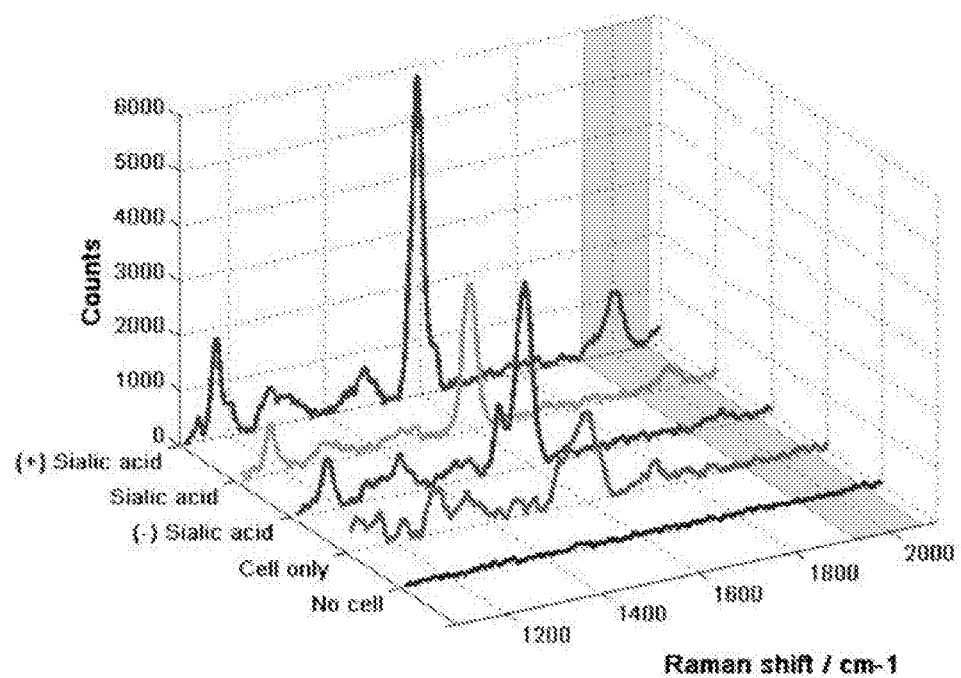
FIG. 9 depicts Raman spectra of prednisolone treated HeLa cell ((+)Sialic acid), PBA treated HeLa cell ((−)Sialic acid), positive control (Sialic acid), negative control (Cell only) and Raman signal from fiber when no cell loaded in fiber.

The Raman spectra of these samples were shown in FIG. 9. Higher intensity at 2,000 cm$^{-1}$ for cells treated with prednisolone was observed to be higher than that of the positive control, suggesting the increased sialic acid expression for treated cells. Given the similarity in chemical structure between phenylboronic acid and DBA that both will bind to sialic acid. As a result, after pre-treatment with PBA in (−)Sialic acid sample, the probability of DBA binding to sialic acid on HeLa cells is lowered. Since DBA contains an alkyne functional group which gives the 2,000 cm$^{-1}$ peak, negligible presence of that peak in Raman spectrum of (−)Sialic acid sample indicate no binding of DBA. Spectrum of the negative control was shown to overlap with that of DBA at wavenumbers below 1,800 cm$^{-1}$, confirming that the intensity of the 2,000 cm$^{-1}$ peak of DBA was uninterrupted. A spectrum was obtained where no cell was loaded into the fiber as a result of their low concentration (and consequently, a lowered probability of observing a cell). Here, no peak was observed in the entire spectrum.

Figure 10A:
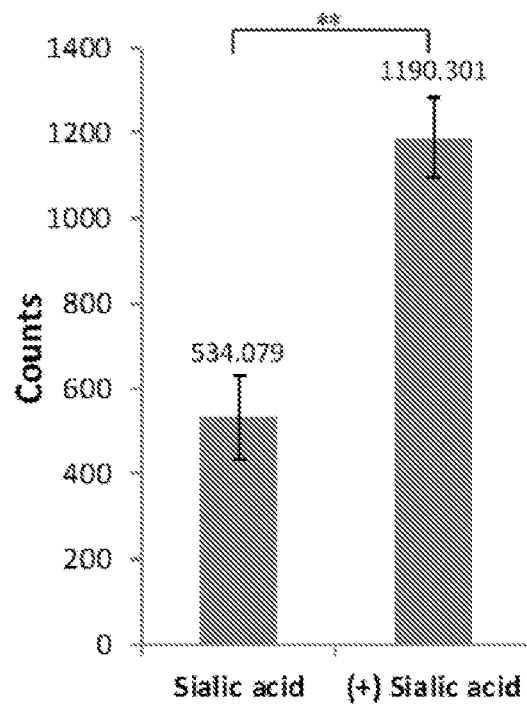
FIG. 10A is a graph showing 2000 cm$^{-1}$ peak intensity of (+)Sialic acid and Sialic acid samples.
Figure 10B:
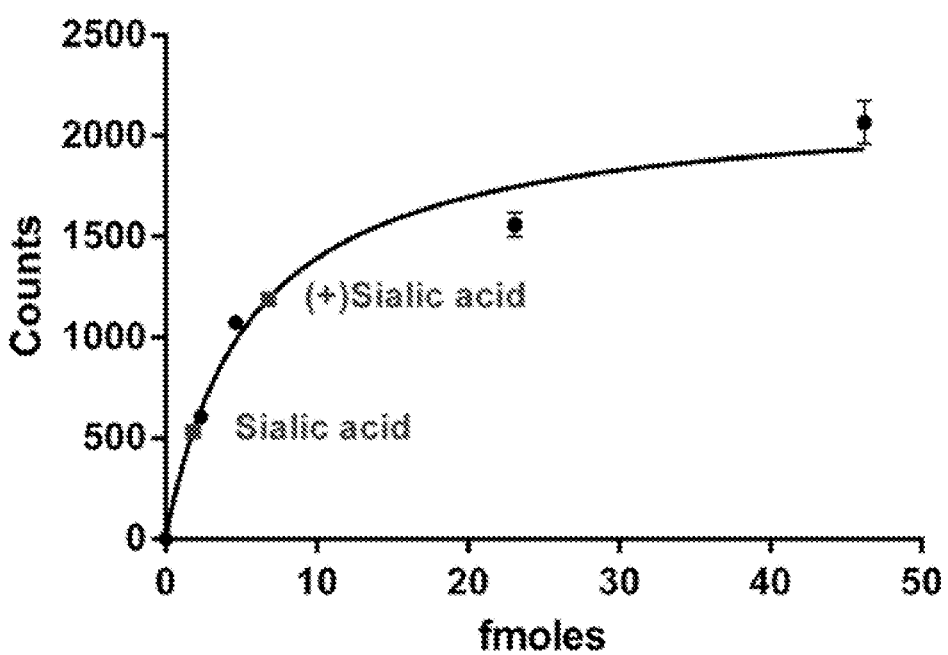
FIG. 10B is a graph showing calculated sialic acid values (two squares for Sialic acid and (+)Sialic acid samples, respectively) from plotted trend line (line) of the calibration points (round).

In order to calculate the amount of sialic acid on cell for Sialic acid and (+)Sialic acid samples, intensity of the 2,000 cm$^{-1}$ peak was obtained from the SERS measurement (FIG. 10A). A calibration trend line was plotted, which clearly represented the correlation between intensity of 2,000 cm$^{-1}$ peak and number of DBA molecules (FIG. 10B). The number of sialic acid molecules may be quantified by estimating the amount of DBA molecules from the trend line as the binding between DBA molecule to the sialic acid molecule is one by one. By estimating the DBA molecules number from calibration curve, the calculated sialic acid amount on a single Hela cell for Sialic acid and (+)Sialic acid samples are 1.822 fmoles and 6.782 fmoles, respectively. This result correlated well with previous reported results, where their values of sialic acid molecules on single cell were derived by calculating the mean value originated from large amount of cells (from $10^5$ to $10^9$ cells).

TABLE 1

Comparison between commercial kit and a method disclosed herein

|  | Commercial kit (Sialic Acid Quantitation Kit, Sigma) | Method disclosed herein (BOIG/SBIC) |
|---|---|---|
| Processing steps | 1. Harvesting and killing cells<br>2. Add a-(2-3,6,8,9)-Neuraminidase, incubate overnight<br>3. Centrifuge cells to get supernatant and diluted with Tris Reaction Buffer<br>4. Add N-Acetylneuraminic Acid Aldolase and incubate for 10 min<br>5. Add 20 ml of the b-NADH Solution and read initial b-NADH value<br>6. Return the reaction mixture to the original tube. Add 1 ml of Lactic Dehydrogenase, incubate in a 37° C. water bath for a minimum of 10 minutes<br>7. Read and record the final value and calculate sialic acid value | 1. Add DBA molecules and culture with cell for 4 hours<br>2. Harvesting cells and mixing with gold nanoparticles<br>3. Pump into fiber for detection<br>4. Calculate sialic acid value |

TABLE 1-continued

Comparison between commercial kit and a method disclosed herein

| | Commercial kit (Sialic Acid Quantitation Kit, Sigma) | Method disclosed herein (BOIG/SBIC) |
|---|---|---|
| Sensitivity | Detection based on large amount of cells | Detection based on single cell |
| Living cell study | no | yes |
| Process Time | slow | fast |
| Sample volume | More than 1 mL | ~50 nL |
| Experimental process | tedious | simple |

TABLE 2

Sialylation changes associated with malignant transformation and tumor progression

| Sialic acid | Linkage | Glycans | Glycan carrier | Type of cancer | hypothesized mechanistic and practical significance |
|---|---|---|---|---|---|
| Sialic acid | Various | Various | Various | Many | Reduction of cell—cell interactions Protection from complement Alteration of interactions with collagen |
| Sialic acid | a2-3Gal | Lewis X/A | Mucins | Most carcinomas | Tumor marker. Poor prognosis. Facilitation of platelet-leukocyte interactions in metastasis |
| Sialic acid | a2-6Gal | N-glycan | Integrins | Some carcinomas | Alteration of integrin function Enhancement of invasion Poor prognosis in some cancers |
| Sialic acid | a2-6GalNAc | Tn | Mucins | Some carcinomas | Enhancement of invasion Tumor marker. Target for immunotherapy |
| Sialic acid | a2-8Sia | N-glycan | N-CAM | Brain tumors, myelomas | Reduction of cell—cell interactions Facilitates metastasis |
| Neu5Gc | Various | Various | Various | Most carcinomas | Accumulated from dietary sources Associated with anti-Neu5Gc antibodies |
| 9-O-Ac | a2-8Sia | GD3 | Ganglioside | Melanomas | Tumor marker. Protects from GD3-mediated apoptosis |
| 9-O-Ac | a2-6GalNAc | O-glycans | Mucins | Leukemias | Prognostic marker |

Abbreviations:
N-CAM, neural cell adhesion molecule;
Tn, Siaa2-3GalNAca-Ser/Thr.

In conclusion, the inventors successfully demonstrated a novel SERS based platform that can detect and quantify sialic acid on single living cancer cells using HC-PCF based system. To the best of their knowledge, this is the first reported SERS-based fiber platform that can accurately quantify components on single living cell. As compared with previously reported sialic acid detection methods, our method is much simpler and easier to perform. More importantly, with combination of the benefits from liquid sample detection capability of HC-PCF, non-interfered 2,000 cm$^{-1}$ peak from DBA and ability of AuNP to provide strong '3D' SERS enhancement, the inventors were able to achieve highly sensitive detection of compounds on a single cell. Given this combination of advantages, the inventors expect that the system may be used in sialic acid detection, and may also be developed into clinical diagnostic tool, which will find broad applications in highly sensitive detection of biomolecules from various types of liquid samples such as blood, serum, plasma, urine, saliva, sweat and tears.

While the present invention has been particularly shown and described with reference to exemplary embodiments thereof, it will be understood by those of ordinary skill in the art that various changes in form and details may be made therein without departing from the spirit and scope of the present invention as defined by the following claims.

The invention claimed is:

1. A method for assessing a health condition of a living cell using surface enhanced Raman spectroscopy (SERS), the method comprising
   a) incubating one or more living cells with an alkyne-containing compound to form one or more modified living cells,
   b) mixing the one or more modified living cells with a SERS-active material to form a mixture,
   c) injecting the mixture into a conduit defined by an inner wall of a hollow core photonic crystal fiber, and
   d) detecting a surface enhanced Raman signal from the mixture in the conduit, which comprises detecting changes in pattern and/or intensity of the surface enhanced Raman signal in a region of 1800 cm$^{-1}$ to 2200 cm$^{-1}$,
   wherein the conduit is dimensioned (i) to accommodate one modified living cell at each location along its length spaced apart from another modified living cell and (ii) for each modified living cell to be surrounded volumetrically with the SERS-active material.

2. The method according to claim 1, wherein incubating the one or more living cells with the alkyne-containing compound comprises incubating the one or more living cells with the alkyne-containing compound for a time period in a range of about 1 hour to about 5 hours.

3. The method according to claim 1, wherein the alkyne-containing compound is selected from the group consisting of an alkyne-modified unsaturated fatty acid, an alkyne-functionalized boronic acid, and combinations thereof.

4. The method according to claim 1, wherein the alkyne-containing compound is selected from the group consisting of linoleamide alkyne, 4-(dihydroxyborophenyl) acetylene, and combinations thereof.

5. The method according to claim 1, wherein the SERS-active material comprises nanoparticles of the SERS-active material.

6. The method according to claim 5, wherein each nanoparticle of the SERS-active material has a diameter in a range from about 5 nm to about 250 nm.

7. The method according to claim 5, wherein each nanoparticle of the SERS-active material has a diameter in a range from about 60 nm to about 100 nm.

8. The method according to claim 5, wherein concentration of the nanoparticles of the SERS-active material in the mixture is in a range of about $1\times10^{10}$ particles/mL to about $1\times10^{12}$ particles/mL.

9. The method according to claim 1, wherein the SERS-active material comprises gold nanoparticles.

10. The method according to claim 1, wherein concentration of the one or more modified living cells in the mixture is in a range of about 20,000 cells/mL to about 30,000 cells/mL.

11. The method according to claim 1, wherein the conduit is dimensioned to accommodate one modified living cell.

12. The method according to claim 1, wherein detecting a surface enhanced Raman signal from the mixture in the conduit comprises directing a radiation into the conduit for a time period in a range of about 8 seconds to about 12 seconds.

13. The method according to claim 1, wherein detecting a surface enhanced Raman signal from the mixture in the conduit comprises collecting the surface enhanced Raman signal in a backscattering geometry.

14. The method according to claim 1, wherein assessing the health condition of the living cell comprises determining presence and/or extent of lipid peroxidation of the living cell.

15. The method according to claim 1, wherein assessing the health condition of the living cell comprises determining presence and/or amount of salic acid on the living cell.

16. The method according to claim 15, wherein amount of the salic acid on the living cell is correlated with surface enhanced Raman signal from the mixture in the conduit.

17. The method according to claim 1, wherein the one or more living cells is contained in a sample and the detection is in vitro.

* * * * *